US008501185B2

(12) United States Patent
Heitner Hansen et al.

(10) Patent No.: US 8,501,185 B2
(45) Date of Patent: Aug. 6, 2013

(54) DIMERIC MOLECULAR COMPLEXES

(75) Inventors: Tara Renee Heitner Hansen, København V (DK); David Light, San Mateo, CA (US); Kirk McLean, Orinda, CA (US); Renate Parry, Oakland, CA (US); Noboru Satozawa, Chiba (JP); Douglas Schneider, Lafayette, CA (US); Marian Seto, Orinda, CA (US)

(73) Assignee: Bayer Healthcare LLC, Whippany, NJ (US)

( * ) Notice: Subject to any disclaimer, the term of this patent is extended or adjusted under 35 U.S.C. 154(b) by 514 days.

(21) Appl. No.: 12/302,283

(22) PCT Filed: May 24, 2007

(86) PCT No.: PCT/EP2007/004601
§ 371 (c)(1),
(2), (4) Date: Nov. 4, 2010

(87) PCT Pub. No.: WO2007/137760
PCT Pub. Date: Dec. 6, 2007

(65) Prior Publication Data
US 2011/0104058 A1    May 5, 2011

Related U.S. Application Data

(60) Provisional application No. 60/808,840, filed on May 25, 2006.

(51) Int. Cl.
| C07K 1/32 | (2006.01) |
| C07K 16/46 | (2006.01) |
| C07K 16/00 | (2006.01) |
| A61K 39/00 | (2006.01) |

(52) U.S. Cl.
USPC ............... 424/178.1; 424/134.1; 424/135.1; 424/192.1; 424/193.1; 530/387.3

(58) Field of Classification Search
None
See application file for complete search history.

(56) References Cited

U.S. PATENT DOCUMENTS

2005/0136049 A1 *   6/2005   Ledbetter et al. .......... 424/132.1

FOREIGN PATENT DOCUMENTS

| WO | WO-94/21676 | 9/1994 |
| WO | WO-00/15651 | 3/2000 |
| WO | WO-2005/017148 | 2/2005 |

OTHER PUBLICATIONS

Yu et al, Investigative Ophthalmology & Visual Science 49(2): 522-527, Feb. 2008.*
Stancovski et al, Proceedings of the National Academy of Science USA 88: 8691-8695, 1991.*
Riemer et al, Mol. Immunol. 42: 1121-1124, 2005.*
Saphire et al, J Mol. Biol 319: 9-16, 2002.*
Mason et al, Molecular Endocrinology 8(3): 325-332, 1994.*
M. Occhino et al.: "Generation and characterization of dimeric small immunoproteins specific for neuroblastoma associated anrigen GD2," International Journal of Molecular Medicine, vol. 14, No. 3, Sep. 2004, pp. 383-388.
M. Bestagno et al.: "Membrane immunoglobulins are stabilized by interchain disulfide bonds occurring within the extracellular membrane-proximal domain," Biochemistry, vol. 40. No. 35, Sep. 4, 2001, pp. 10686-10692.
D. Zhu et al.: "A novel human immunoglobulin Fc gamma Fc epsilon bifunctional fusion protein inhibits Fc epsilon RI-mediated degranulation," Nature Medicine, vol. 8, No. 5, May 2002, pp. 518-521.
F. Batista et al.: "Characterization of the human immunoglobulin epsilon mRNAs and their polyadenylation sites," Nucleic Acids Research, vol. 23, No. 23, Dec. 11, 1995, pp. 4805-4811.
R. Parry et al.: "Identification of a novel prostate tumor target, Mindin/RG-1, for antibody-based radiotherapy of prostate cancer," Cancer Research, vol. 65, No. 18, Sep. 15, 2005, pp. 8397-8405.

* cited by examiner

*Primary Examiner* — Phuong Huynh
(74) *Attorney, Agent, or Firm* — Bayer Healthcare LLC

(57) ABSTRACT

Dimeric molecular complexes useful for diagnostics and therapeutics.

27 Claims, 20 Drawing Sheets

FIG. 1A
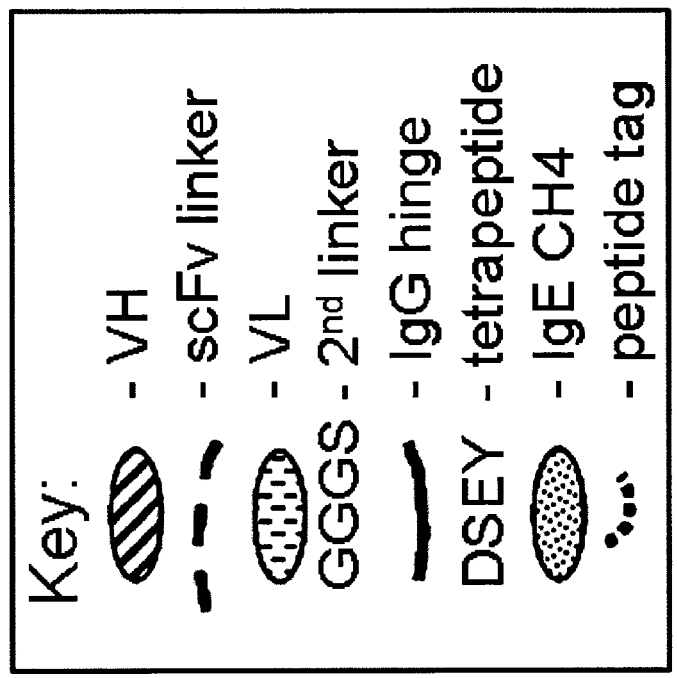
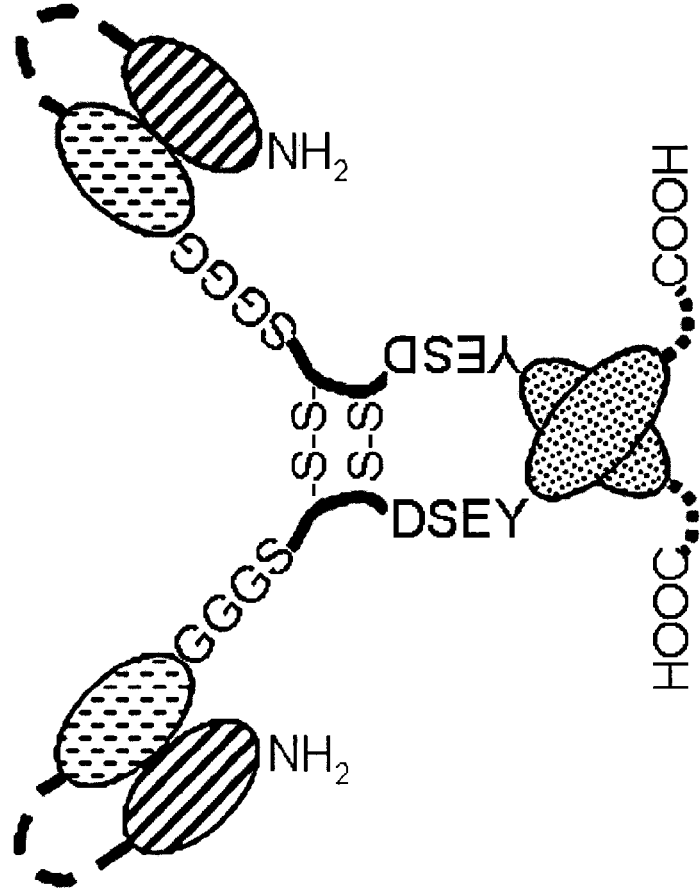

Fab dimer molecules:
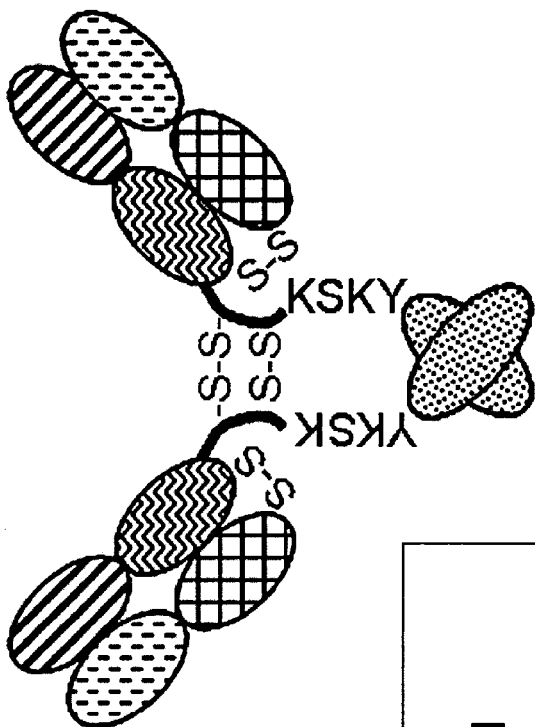
ValPheLeuPhe → LysSerLysTyr (sites for conjugation)
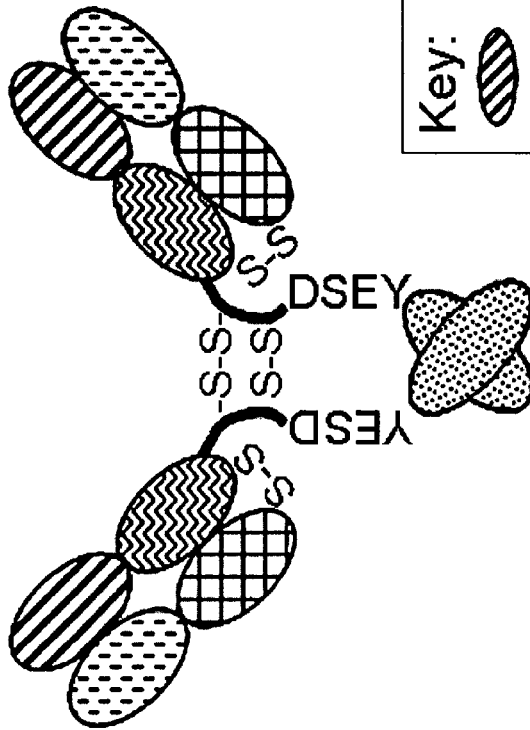
ValPheLeuPhe → AspSerGluTyr (solubility)
FIG. 1B

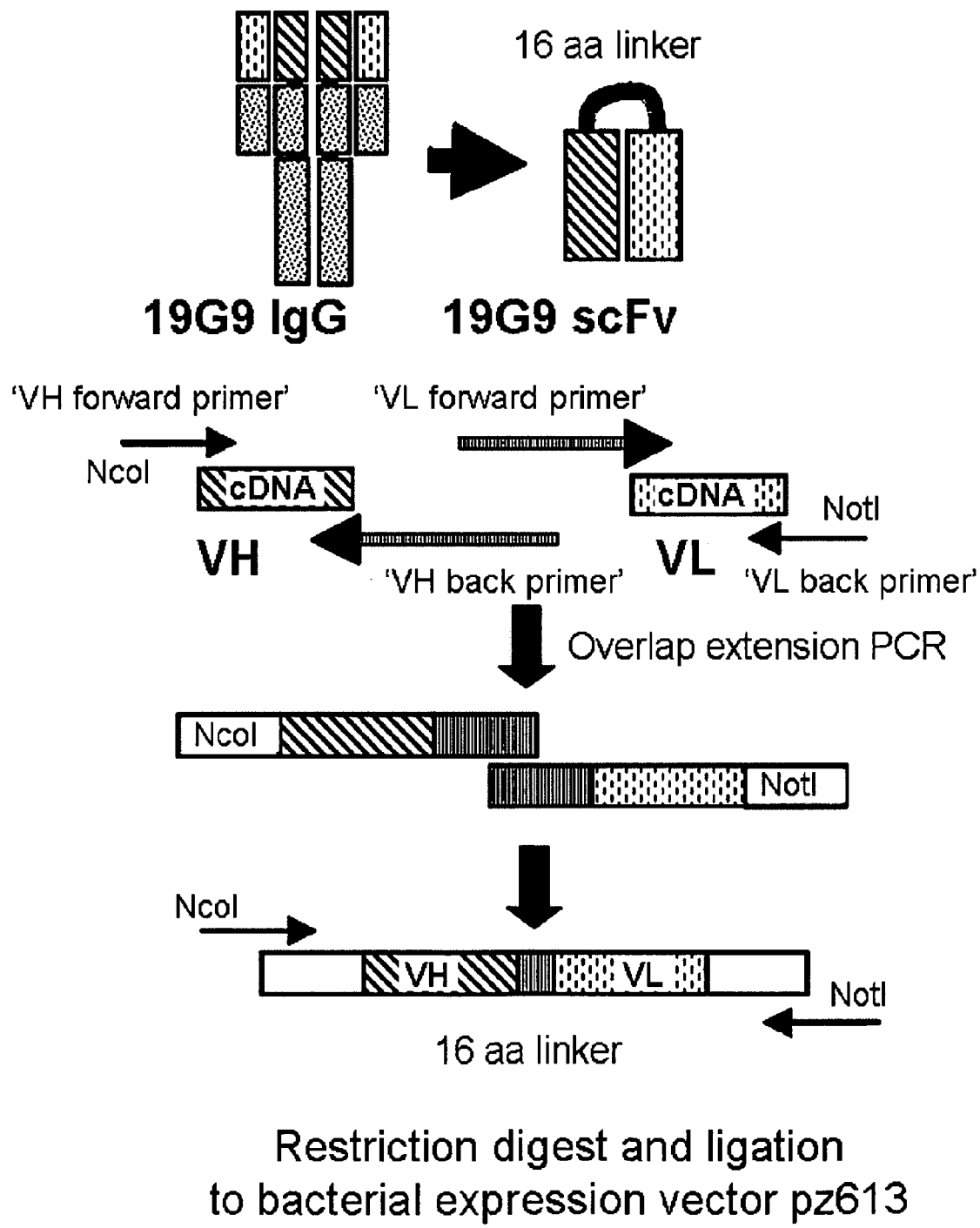

FIG. 5A

"Wild type" 19G9 scFv dimeric molecular complex sequences
DNA (SEQ ID NO:4) and protein

```
                    NcoI           PvuII
                    ------         --------
                              Q  V  Q  L  V  Q  S  G  G  G  L  V  Q  P  G  G  S  L  R  L  S  C  A  G
  1   CTTTCTATGC GGCCCAGCCG GCCATGGCCC AGGTTCAGCT GGTGCAGTCT GGGGGAGGCT TGGTACAACC TGGGGGTCC CTGAGACTCT CCTGTGCAGC
      · S  G  F   T  F  S   Y  V  M    H  W  L    R  Q  A  P    G  K  G    L  E  W    V  S  V    I  G  T  G  G  V  T
 101  CTCTGGATTC ACCTTCAGTA GCTATGTTAT GCACTGGCTT CGCCAGGCTC CAGGAAAGGG TCTGGAGTGG GTATCAGTTA TTGGTACTGG TGGTGTCACA
       H  Y  A  D   S  V  K   G  R  F   T  I  S  R    D  N  A   K  N  S    L  Y  L  Q    M  N  S    L  R  A    E  D  T  A
 201  CACTATGCAG ACTCCGTGAA GGGCCGATTC ACCATCTCCA GAGACAATGC CAAGAACTCC TTGTATCTTC AAATGAACAG CCTGAGAGCC GAGGACACGG
      · V  Y  Y   C  A  R   W  G  Y  Y   G  S  G    S  Y  E    N  D  A  F    D  I  W   G  Q  G    T  M  V  T  V  S  S  ·
 301  CTGTGTATTA CTGTGCAAGA TGGGGTTACT ATGGTTCGGG GAGTTATGAG AATGATGCTT TTGATATCTG GGGCCAAGGG ACAATGGTCA CCGTCTCTTC
                                                                        BamHI
                                                                        ----------
                                      G  G  G  G   S  G  G   G  G  S   G  G  G  G  S    E  I  V    L  T  Q  S    P  G  T    L  S  L
 401  AGGTGGTGGT GGTTCTGGTG GTGGTGGTTC TGGCGGCGGC GGCTCCGTC GTGGTGGATC CGAAATTGTG TTGACGCAGT CTCCAGGCAC CCTGTCTTTG
                                                       PstI                                                         KpnI
                                                       ------                                                       -------
        S  P  G  E   R  A  T   L  S  C    R  A  S   Q  S  V    S  S  S  Y    L  A  W    Y  Q  Q  K    P  G  Q    A  P  R  L  ·
 501  TCTCCAGGGG AAAGAGCCAC CCTCTCCTGC AGGGCCAGTC AGAGTGTTAG CAGCAGCTAC TTAGCCTGG ACCAGCAGAA ACCTGGCCAG GCTCCCAGGC
        ·  L  I  Y   G  A  S   S  R  A  T    G  I  P   D  R  F    S  G  S    G  S  G  T   D  F  T    L  T  I  S    R  L  E
 601  TCCTCATCTA TGGTGCATCC AGCAGGGCCA CTGGCATCCC AGACAGGTTC AGTGGCAGTG GGTCTGGGAC AGACTTCACT CTCACCATCA GCAGACTGGA

IgG1_hinge_splice_bk
```

```
                                                                                    IgG1hinj_IgECH4_bk_a
                                                                                    ~~~~~~~~~~~~~~~~~~~
                                                                                                NotI
                                                                                                --------
        · P  E  D   F  A  V  Y   Y  C  Q    Q  Y  S   S  S  L  T    F  G  G    G  T  K    V  E  I  K    A  A  A    G  G  G
 701  GCCTGAAGAT TTTGCAGTGT ATTACTGTCA GCAGTATAGT AGCTCGGTCA CTTTCGGCGG GGGGACCAAG GTGGAGATCA AAGCGGCCGC AGGCGGCGGT
                                     IgG1_hinge_splice_bk
IgG1hinj_IgECH4_bk_a                                                   IgECH4_bk_a
~~~~~~~~~~~~~~~~~~~                                                    ~~~~~~~~~~~
        G  S  T  H   T  C  P   P  C  P   A  P  E  L    L  G  G    P  S  V   F  L  F  P    P  R  A    A  P  E    V  Y  A  F  ·
 801  GGTTCCACTC ACACATGCCC ACCGTGCCCA GCACCTGAAC TCCTGGGGGG ACCGTCAGTC TTCCTCTTCC CCCCGCGTGC TGCCCCGGAA GTCTATGCCT
        · A  T  F   E  W  P   G  S  R  D   K  R  T    L  A  G    L  I  Q  N    F  M  P    E  D  I    S  V  Q  W    L  H  N  ·
 901  TTGCGACGCC GGAGTGGCCG GGGAGCCGGG ACAAGCGCAC CCTCGCCTGC CTGATCCAGA ACTTCATGCC TGAGGACATC TCGGTGCAGT GGCTGCACAA
        · E  V  Q   L  P  D  A    E  H  S    T  T  Q    P  R  K  T   K  G  S    G  F  F    V  F  S  R    L  E  V    T  R  A
1001  CGAGGTGCAG CTCCCGGACG CCGGGCACAG CACGACGCAG CCCGCAAGA CCAAGGGCTC CGGCTTCTTC GTCTTCAGCC GGCTGGAGGT GACCAGGGCC
                                                                                                                IgECH4_for_a
                                                                                                                ~~~~~~~~~~~~
        E  W  E  Q   K  D  E   F  I  C   R  A  V  H    E  A  A    S  P  S   Q  T  V  Q    R  A  V    S  V  N  P    G  K  G  ·
1101  GAATGGGAGC AGAAAGATGA GTTCATCTGC CGTGCAGTCC ATGAGGCAGC GAGCCCCTCA CAGACCGTCC AGCGAGCGGT GTCTGTAAAT CCCGGTAAAG
        IgECH4_for_a
        ------------
        SgrAI  BamHI
        -----  -----
        · A  P  V   P  Y  P   D  P  L   E  P  R  A   A  *
1201  GTGCCCCGGT GCCCTATCCC GATCCGCTGG AACCGCGTGC CGCATAGACT
```

Amino acid sequence of 19G9 scFv dimeric molecular complex
"wild type" – SEQ ID NO:3

QVQLVQSGGGLVQPGGSLRLSCAGSGFTFSSYVMHWLRQAPGKGLEWVSVIGTGGVTHY

ADSVKGRFTISRDNAKNSLYLQMNSLRAEDTAVYYCARWGYYGSGSYENDAFDIWGQGTMVT

VSS*GGGGSGGGGSGGGGSGGGGS*EIVLTQSPGTLSLSPGERATLSCRASQSVSSSY

LAWYQQKPGQAPRLLIYGASSRATGIPDRFSGSGSGTDFTLTISRLEPEDFAVYYCQQYSSS

LTFGGGTKVEIKAAAGGGGS *THTCPPCPAPELLGGPS*VFLF*PPRAAPEVYAFATPEWPGSRD*

KRTLACLIQNFMPEDISVQWLHNEVQLPDARHSTTQPRKTKGSGFFVFSRLEVTRAEWEQKD

EFICRAVHEAASPSQTVQRAVSVNPGK*GAPVPYPDPLEPRAA*

FIG. 5B

Mutant 19G9 dimeric molecular complex sequences
DNA (SEQ ID NO:2) and protein

```
                              NcoI            PvuII
                         Q  V  Q  L     V  Q  S  G  G  G  L  V  Q  P  G  G  S  L  R  L  S  C  A  G
   1 CTTTCTATGC GGCCCAGCCG GCCATGGCCC AGGTTCAGCT GGTGCAGTCT GGGGGAGGCT TGGTACAACC TGGGGGGTCC CTGAGACTCT CCTGTGCAGG
     ·  S  G  F  T  F  S  S  Y  V  M  H  W  L  R  Q  A  P  G  K  G  L  E  W  V  S  V  I  G  T  G  G  V  T·
  101 CTCTGGATTC ACCTTCAGTA GCTATGTTAT GCACTGGCTT CGCCAGGCTC CAGGAAAAGG TCTGGAGTGG GTATCAGTTA TTGGTACTGG TGGTGTCACA
     H  Y  A  D  S  V  K  G  R  F  T  I  S  R  D  N  A  K  N  S  L  Y  L  Q  M  N  S  L  R  A  E  D  T  A
  201 CACTATGCAG ACTCCGTGAA GGGCCGATTC ACCATCTCCA GAGACAATGC CAAGAACTCC TTGTATCTTC AAATGAACAG CCTGAGAGCC GAGGACACGG
     ·  V  Y  Y  C  A  R  W  G  Y  Y  G  S  G  S  Y  E  N  D  A  F  D  I  W  G  Q  G  T  M  V  T  V  S  S·
  301 CTGTGTATTA CTGTGCAAGA TGGGGTTACT ATGGTTCGGG GAGTTATGAG AATGATGCTT TTGATATCTG GGGCCAAGGG ACAATGGTCA CCGTCTCTTC
                                                                     BamHI
     ·  G  G  G  G  S  G  G  G  G  S  G  G  G  G  S  E  I  V  L  T  Q  S  P  G  T  L  S  L
  401 AGGTGGTGGT GGTTCTGGTG GTGGTGGTTC TGGCGGCGGC GGCTCCGGTG GTGGTGGATC CGAAATTGTG TTGACGCAGT CTCCAGGCAC CCTGTCTTTG
                                                               PstI                  KpnI
     ·  S  P  G  E  R  A  T  L  S  C  R  A  S  Q  S  V  S  S  S  Y  L  A  W  Y  Q  Q  K  P  G  Q  A  P  R  L·
  501 TCTCCAGGGG AAAGAGCCAC CCTCTCCTGC AGGGCCAGTC AGAGTGTTAG CAGCAGCTAC TTAGCCTGGT ACCAGCAGAA ACCTGGCCAG GCTCCCAGGC
     ·  L  I  Y  G  A  S  S  R  A  T  G  I  P  D  R  F  S  G  S  G  S  G  T  D  F  T  L  T  I  S  R  L  E·
  601 TCCTCATCTA TGGTGCATCC AGCAGGGCCA CTGGCATCCC AGACAGGTTC AGTGGCAGTG GGTCTGGGAC AGACTTCACT CTCACCATCA GCAGACTGGA
IgG1_hinge_splice_bk
                                                                                             IgG1hing_IgECH4_bk_a NotI
     ·  P  E  D  F  A  V  Y  Y  C  Q  Q  Y  S  S  S  L  T  F  G  G  G  T  K  V  E  I  K  A  A  A  G  G
  701 GCCTGAAGAT TTTGCAGTGT ATTACTGTCA GCAGTATAGT AGCTCGCTCA CTTTCGGCGG GGGGACCAAG GTGGAGATCA AAGCGGCCGC AGGCGGCGGT
                                                                       IgG1_hinge_splice_bk
IgG1hing_IgECH4_bk_a
     G  S  T  H  T  C  P  P  C  P  A  P  E  L  L  G  G  P  S  D  S  E  Y  P  R  A  A  P  E  V  Y  A  F·
  801 GGTTCCACTC ACACATGCCC ACCGTGCCCA GCACCTGAAC TCCTGGGGGG ACCGTCAGAC AGCGAGTACC CCCGGCGTGC TGCCCCGGAA GTCTATGCGT
     ·  A  T  P  E  W  P  G  S  R  D  K  R  T  L  A  C  L  I  Q  N  F  M  P  E  D  I  S  V  Q  W  L  H  N·
  901 TTGCGACGCC GGAGTGGCCG GGAGCCGGG ACAAGCGCAC CCTCGCCTGC CTGATCCAGA ACTTCATGCC TGAGGACATC TCGGTGCAGT GGCTGCACAA
     ·  E  V  Q  L  P  D  A  R  H  S  T  T  Q  P  R  K  T  K  G  S  G  F  F  V  F  S  R  L  E  V  T  R  A·
 1001 CGAGGTGCAG CTCCCGGACG CCCGGCACAG CACGACGCAG CCCCGCAAGA CCAAGGGCTC CGGCTTCTTC GTCTTCAGCC GCCTGGAGGT GACCAGGGCC
                                                                                                        IgECH4_for_a
     E  W  E  Q  K  D  E  F  I  C  R  A  V  H  E  A  A  S  P  S  Q  T  V  Q  R  A  V  S  V  N  P  G  K·
 1101 GAATGGGAGC AGAAAGATGA GTTCATCTGC CGTGCAGTCC ATGAGGCAGC GAGCCCCTCA CAGACCGTCC AGCGAGCGGT GTCTGTAAAT CCCGGTAAAG
IgECH4_for_a
             SgrAI      BamHI
     ·  A  P  V  P  Y  P  D  P  L  E  P  R  A  A  *
 1201 GTGCCCCCGT GCCGTATCCC GATCCGCTGG AACCCCGTGC CGCATAGACT
```

Amino acid sequence of 19G9 scFv dimeric molecular complex
hydrophilic mutant – SEQ ID NO:1

*QVQLVQSGGGLVQPGGSLRLSCAGSGFTFSSYVMHWLRQAPGKGLEWVSVIGTGGVTHY*

*ADSVKGRFTISRDNAKNSLYLQMNSLRAEDTAVYYCARWGYYGSGSYENDAFDIWGQGTMVT*

*VSS*GGGGSGGGGSGGGGSGGGGSEIVLTQSPGTLSLSPGERATLSCRASQSVSSSY

LAWYQQKPGQAPRLLIYGASSRATGIPDRFSGSGSGTDFTLTISRLEPEDFAVYYCQQYSSS

LTFGGGTKVEIKAAAGGGS *THTCPPCPAPELLGGPS*<u>DSEY</u>*PPRAAPEVYAFATPEWPGSRD*

*KRTLACLIQNFMPEDISVQWLHNEVQLPDARHSTTQPRKTKGSGFFVFSRLEVTRAEWEQKD*

*EFICRAVHEAASPSQTVQRAVSVNPGK*<u>*GAPVPYPDPLEPRAA*</u>

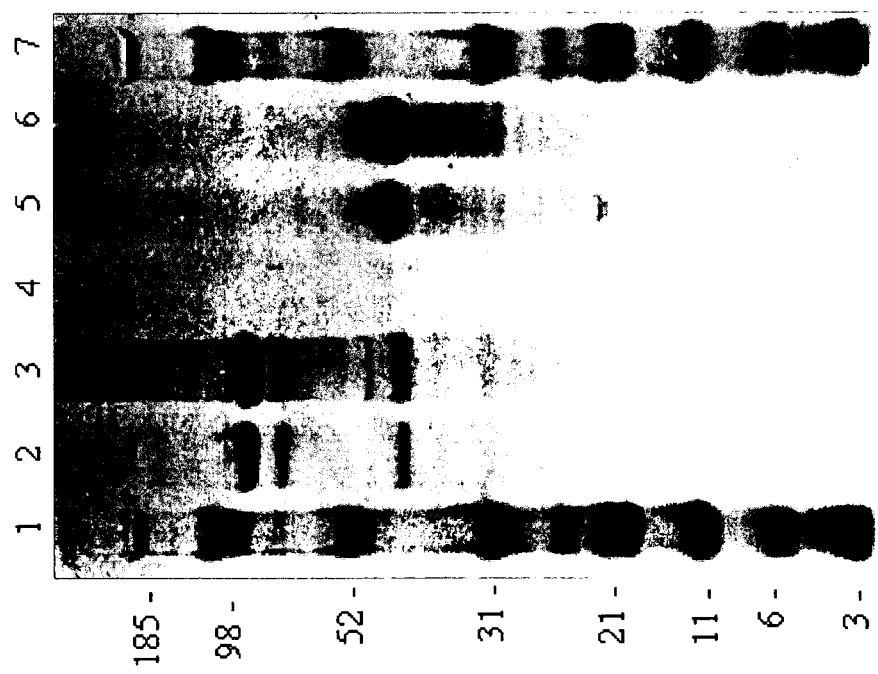

SEQUENCE LISTING

<160> NUMBER OF SEQ ID NOS: 73

<210> SEQ ID NO 1
<211> LENGTH: 405
<212> TYPE: PRT
<213> ORGANISM: artificial
<220> FEATURE:
<223> OTHER INFORMATION: 19G9scFv dimeric construct, hydrophilic mutant
      hinge

<400> SEQUENCE: 1

Gln Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Val Met His Trp Leu Arg Gln Ala Pro Gly Lys Gly Leu Glu Trp Val
        35                  40                  45

Ser Val Ile Gly Thr Gly Gly Val Thr His Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Tyr Tyr Gly Ser Gly Ser Tyr Glu Asn Asp Ala Phe Asp
            100                 105                 110

Ile Trp Gly Gln Gly Thr Met Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Glu Ile Val Leu Thr Gln Ser Pro Gly Thr Leu Ser Leu Ser Pro Gly
145                 150                 155                 160

Glu Arg Ala Thr Leu Ser Cys Arg Ala Ser Gln Ser Val Ser Ser Ser
                165                 170                 175

Tyr Leu Ala Trp Tyr Gln Gln Lys Pro Gly Gln Ala Pro Arg Leu Leu
            180                 185                 190

Ile Tyr Gly Ala Ser Ser Arg Ala Thr Gly Ile Pro Asp Arg Phe Ser
        195                 200                 205

Gly Ser Gly Ser Gly Thr Asp Phe Thr Leu Thr Ile Ser Arg Leu Glu
    210                 215                 220

Pro Glu Asp Phe Ala Val Tyr Tyr Cys Gln Gln Tyr Ser Ser Ser Leu
225                 230                 235                 240

Thr Phe Gly Gly Gly Thr Lys Val Glu Ile Lys Ala Ala Ala Gly Gly
                245                 250                 255

Gly Gly Ser Thr His Thr Cys Pro Pro Cys Pro Ala Pro Glu Leu Leu
            260                 265                 270

Gly Gly Pro Ser Asp Ser Glu Tyr Pro Pro Arg Ala Ala Pro Glu Val
        275                 280                 285

Tyr Ala Phe Ala Thr Pro Glu Trp Pro Gly Ser Arg Asp Lys Arg Thr
    290                 295                 300

Leu Ala Cys Leu Ile Gln Asn Phe Met Pro Glu Asp Ile Ser Val Gln
305                 310                 315                 320

Trp Leu His Asn Glu Val Gln Leu Pro Asp Ala Arg His Ser Thr Thr
                325                 330                 335

Gln Pro Arg Lys Thr Lys Gly Ser Gly Phe Phe Val Phe Ser Arg Leu
            340                 345                 350

Glu Val Thr Arg Ala Glu Trp Glu Gln Lys Asp Glu Phe Ile Cys Arg
            355                 360                 365

Ala Val His Glu Ala Ala Ser Pro Ser Gln Thr Val Gln Arg Ala Val
        370                 375                 380

Ser Val Asn Pro Gly Lys Gly Ala Pro Val Pro Tyr Pro Asp Pro Leu
385                 390                 395                 400

Glu Pro Arg Ala Ala
            405

<210> SEQ ID NO 2
<211> LENGTH: 1224
<212> TYPE: DNA
<213> ORGANISM: artificial
<220> FEATURE:
<223> OTHER INFORMATION: 19G9scFv fusion protein, hydrophilic mutant
      hinge

<400> SEQUENCE: 2
atggcccagg ttcagctggt gcagtctggg ggaggcttgg tacaacctgg ggggtccctg      60
agactctcct gtgcaggctc tggattcacc ttcagtagct atgttatgca ctggcttcgc     120
caggctccag aaaaggtctg gagtgggta tcagttattg gtactggtgg tgtcacacac      180
tatgcagact ccgtgaaggg ccgattcacc atctccagag acaatgccaa gaactccttg     240
tatcttcaaa tgaacagcct gagagccgag gacacggctg tgtattactg tgcaagatgg     300
ggttactatg gttcggggag ttatgagaat gatgcttttg atatctgggg ccaagggaca     360
atggtcaccg tctcttcagg tggtggtggt tctggtggtg gtggttctgg cggcggcggc     420
tccggtggtg gtggatccga aattgtgttg acgcagtctc caggcaccct gtctttgtct     480
ccaggggaaa gagccaccct ctcctgcagg gccagtcaga gtgttagcag cagctactta     540
gcctggtacc agcagaaacc tggccaggct cccaggctcc tcatctatgg tgcatccagc     600
agggccactg gcatcccaga caggttcagt ggcagtgggt ctgggacaga cttcactctc     660
accatcagca gactggagcc tgaagatttt gcagtgtatt actgtcagca gtatagtagc     720
tcgctcactt tcggcggggg gaccaaggtg gagatcaaag cggccgcagg cggcggtggt     780
tccactcaca catgcccacc gtgcccagca cctgaactcc tggggggacc gtcagacagc     840
gagtaccccc gcgtgctgc cccggaagtc tatgcgtttg cgacgccgga gtggccgggg      900
agtcgggaca gcgcaccct cgcctgcctg atccagaact tcatgcctga ggacatctcg      960
gtgcagtggc tacacaacga ggtgcagctc ccggacgccc ggcacagcac gacgcagccc    1020
cgcaagacca agggctccgg cttcttcgtc ttcagccgcc tggaggtgac cagggccgaa    1080
tgggagcaga aagatgagtt catctgccgt gcagtccatg aggcagcgag ccccctcacag   1140 accgtccagc gagcggtgtc tgtaaatccc ggtaaaggtg cgccggtgcc gtatccggat    1200
ccgctggaac cgcgtgccgc atag                                          1224

<210> SEQ ID NO 3
<211> LENGTH: 405
<212> TYPE: PRT
<213> ORGANISM: artificial
<220> FEATURE:
<223> OTHER INFORMATION: IgE CH4 dimerization domain, wild-type hinge

<400> SEQUENCE: 3

Gln Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr 20                  25                  30
Val Met His Trp Leu Arg Gln Ala Pro Gly Lys Gly Leu Glu Trp Val
            35                  40                  45

Ser Val Ile Gly Thr Gly Gly Val Thr His Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                85                  90                  95

Arg Trp Gly Tyr Tyr Gly Ser Gly Ser Tyr Glu Asn Asp Ala Phe Asp
                100                 105                 110

Ile Trp Gly Gln Gly Thr Met Val Thr Val Ser Ser Gly Gly Gly Gly
            115                 120                 125

Ser Gly Gly Gly Gly Ser Gly Gly Gly Ser Gly Gly Gly Gly Ser
            130                 135                 140

Glu Ile Val Leu Thr Gln Ser Pro Gly Thr Leu Ser Leu Ser Pro Gly
145                 150                 155                 160

Glu Arg Ala Thr Leu Ser Cys Arg Ala Ser Gln Ser Val Ser Ser Ser
                165                 170                 175

Tyr Leu Ala Trp Tyr Gln Gln Lys Pro Gly Gln Ala Pro Arg Leu Leu
                180                 185                 190

Ile Tyr Gly Ala Ser Ser Arg Ala Thr Gly Ile Pro Asp Arg Phe Ser
                195                 200                 205

Gly Ser Gly Ser Gly Thr Asp Phe Thr Leu Thr Ile Ser Arg Leu Glu
            210                 215                 220

Pro Glu Asp Phe Ala Val Tyr Tyr Cys Gln Gln Tyr Ser Ser Ser Leu
225                 230                 235                 240

Thr Phe Gly Gly Gly Thr Lys Val Glu Ile Lys Ala Ala Gly Gly
                245                 250                 255

Gly Gly Ser Thr His Thr Cys Pro Pro Cys Pro Ala Pro Glu Leu Leu
            260                 265                 270

Gly Gly Pro Ser Val Phe Leu Phe Pro Pro Arg Ala Ala Pro Glu Val
            275                 280                 285

Tyr Ala Phe Ala Thr Pro Glu Trp Pro Gly Ser Arg Asp Lys Arg Thr
            290                 295                 300

Leu Ala Cys Leu Ile Gln Asn Phe Met Pro Glu Asp Ile Ser Val Gln
305                 310                 315                 320

Trp Leu His Asn Glu Val Gln Leu Pro Asp Ala Arg His Ser Thr Thr
                325                 330                 335

Gln Pro Arg Lys Thr Lys Gly Ser Gly Phe Phe Val Phe Ser Arg Leu
                340                 345                 350

Glu Val Thr Arg Ala Glu Trp Glu Gln Lys Asp Glu Phe Ile Cys Arg
                355                 360                 365

Ala Val His Glu Ala Ala Ser Pro Ser Gln Thr Val Gln Arg Ala Val
                370                 375                 380

Ser Val Asn Pro Gly Lys Gly Ala Pro Val Pro Tyr Pro Asp Pro Leu
385                 390                 395                 400

Glu Pro Arg Ala Ala
                405

<210> SEQ ID NO 4
<211> LENGTH: 1224
<212> TYPE: DNA
<213> ORGANISM: artificial
<220> FEATURE:

<223> OTHER INFORMATION: 19G9scFv dimeric construct, wild-type hinge

<400> SEQUENCE: 4

```
atggcccagg ttcagctggt gcagtctggg ggaggcttgg tacaacctgg ggggtccctg    60
agactctcct gtgcaggctc tggattcacc ttcagtagct atgttatgca ctggcttcgc   120
caggctccag gaaaaggtct ggagtgggta tcagttattg gtactggtgg tgtcacacac   180
tatgcagact ccgtgaaggg ccgattcacc atctccagag acaatgccaa gaactccttg   240
tatcttcaaa tgaacagcct gagagccgag gacacggctg tgtattactg caagatgg    300
ggttactatg gttcggggag ttatgagaat gatgcttttg atatctgggg ccaagggaca   360
atggtcaccg tctcttcagg tggtggtggt tctggtggtg gtggttctgg cggcggcggc   420
tccggtggtg gtggatccga aattgtgttg acgcagtctc caggcaccct gtctttgtct   480
ccaggggaaa gagccaccct ctcctgcagg gccagtcaga gtgttagcag cagctactta   540
gcctggtacc agcagaaacc tggccaggct cccaggctcc tcatctatgg tgcatccagc   600
agggccactg gcatcccaga caggttcagt ggcagtgggt ctgggacaga cttcactctc   660
accatcagca gactggagcc tgaagatttt gcagtgtatt actgtcagca gtatagtagc   720
tcgctcactt tcggcggggg gaccaaggtg gagatcaaag cggccgcagg cggcggtggt   780
tccactcaca catgcccacc gtgcccagca cctgaactcc tggggggacc gtcagtcttc   840
ctcttccccc cgcgtgctgc cccggaagtc tatgcgtttg cgacgccgga gtggccgggg   900
agtcgggaca gcgcaccct cgcctgcctg atccagaact tcatgcctga ggacatctcg   960
gtgcagtggc tacacaacga ggtgcagctc ccggacgccc ggcacagcac gacgcagccc  1020
cgcaagacca aggctccgg cttcttcgtc ttcagccgcc tggaggtgac cagggccgaa  1080
tgggagcaga aagatgagtt catctgccgt gcagtccatg aggcagcgag ccctcacag   1140
accgtccagc gagcggtgtc tgtaaatccc ggtaaaggtg cgccggtgcc gtatccggat  1200
ccgctggaac cgcgtgccgc atag                                         1224
```

<210> SEQ ID NO 5
<211> LENGTH: 21
<212> TYPE: PRT
<213> ORGANISM: artificial
<220> FEATURE:
<223> OTHER INFORMATION: hydrophlic mutant hinge construct

<400> SEQUENCE: 5

Thr His Thr Cys Pro Pro Cys Pro Ala Pro Glu Leu Leu Gly Gly Pro
1               5                   10                  15

Ser Asp Ser Glu Tyr
            20

<210> SEQ ID NO 6
<211> LENGTH: 110
<212> TYPE: PRT
<213> ORGANISM: artificial
<220> FEATURE:
<223> OTHER INFORMATION: IgE CH4 domain of dimeric molecular complex

<400> SEQUENCE: 6

Pro Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
        35                  40                  45

Pro Asp Ala Arg His Ser Thr Thr Gln Pro Arg Thr Lys Gly Ser
    50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Lys
            100                 105                 110

<210> SEQ ID NO 7
<211> LENGTH: 21
<212> TYPE: PRT
<213> ORGANISM: artificial
<220> FEATURE:
<223> OTHER INFORMATION: lysine variant-mutant hinge region construct

<400> SEQUENCE: 7

Thr His Thr Cys Pro Pro Cys Pro Ala Pro Glu Leu Leu Gly Gly Pro
1               5                   10                  15

Ser Lys Ser Lys Tyr
            20

<210> SEQ ID NO 8
<211> LENGTH: 20
<212> TYPE: PRT
<213> ORGANISM: artificial
<220> FEATURE:
<223> OTHER INFORMATION: linker

<400> SEQUENCE: 8

Gly Gly Gly Gly Ser Gly Gly Gly Ser Gly Gly Gly Ser Gly
1               5                   10                  15

Gly Gly Gly Ser
            20

<210> SEQ ID NO 9
<211> LENGTH: 40
<212> TYPE: DNA
<213> ORGANISM: artificial
<220> FEATURE:
<223> OTHER INFORMATION: ATG001 primer

<400> SEQUENCE: 9
ccgtcagtct tcctcttccc cccgcgtgct gccccggaag                          40

<210> SEQ ID NO 10
<211> LENGTH: 31
<212> TYPE: DNA
<213> ORGANISM: artificial
<220> FEATURE:
<223> OTHER INFORMATION: ATG002 primer

<400> SEQUENCE: 10
ttcctcttcc cccgcgtgc tgccccggaa g                                    31

<210> SEQ ID NO 11
<211> LENGTH: 40
<212> TYPE: DNA
<213> ORGANISM: artificial
<220> FEATURE:
<223> OTHER INFORMATION: ATG003 primer

<400> SEQUENCE: 11
cggatacggc accggcgcac ctttaccggg atttacagac                          40

<210> SEQ ID NO 12
<211> LENGTH: 86
<212> TYPE: DNA
<213> ORGANISM: artificial
<220> FEATURE:
<223> OTHER INFORMATION: ATG004 primer

<400> SEQUENCE: 12
cggcggtggt tccactcaca catgcccacc gtgcccagca cctgaactcc tgggggacc      60 gtcagtcttc ctcttccccc cgcgtg                                          86

<210> SEQ ID NO 13
<211> LENGTH: 36
<212> TYPE: DNA
<213> ORGANISM: artificial
<220> FEATURE:
<223> OTHER INFORMATION: ATG006 primer

<400> SEQUENCE: 13
agatcaaagc ggccgcaggc ggcggtggtt ccactc                               36

<210> SEQ ID NO 14
<211> LENGTH: 113
<212> TYPE: DNA
<213> ORGANISM: artificial
<220> FEATURE:
<223> OTHER INFORMATION: ATG019 primer

<400> SEQUENCE: 14
caaagcggcc gcaggcggcg gtggttccac tcacacatgc ccaccgtgcc cagcacctga     60
actcctgggg ggaccgtcag acagcgagta ccccccgcgt gctgccccgg aag           113

<210> SEQ ID NO 15
<211> LENGTH: 41
<212> TYPE: DNA
<213> ORGANISM: artificial
<220> FEATURE:
<223> OTHER INFORMATION: VH forward primer

<400> SEQUENCE: 15
gcggcccagc cggccatggc ccaggttcag ctggtgcagt c                         41

<210> SEQ ID NO 16
<211> LENGTH: 66
<212> TYPE: DNA
<213> ORGANISM: artificial
<220> FEATURE:
<223> OTHER INFORMATION: VH back primer

<400> SEQUENCE: 16
ccaccggagc cgccgccgcc agaaccacca ccaccagaac caccaccacc tgaagagacg     60
gtgacc                                                                66

<210> SEQ ID NO 17
<211> LENGTH: 50
<212> TYPE: DNA
<213> ORGANISM: artificial
<220> FEATURE:
<223> OTHER INFORMATION: VL forward primer

<400> SEQUENCE: 17
ggcggcggcg gctccggtgg tggtggatcc gaaattgtgt tgacgcagtc                50

```
<210> SEQ ID NO 18
<211> LENGTH: 28
<212> TYPE: DNA
<213> ORGANISM: artificial
<220> FEATURE:
<223> OTHER INFORMATION: VL back primer

<400> SEQUENCE: 18
gcggccgctt tgatctccac cttggtcc                                          28

<210> SEQ ID NO 19
<211> LENGTH: 234
<212> TYPE: PRT
<213> ORGANISM: artificial
<220> FEATURE:
<223> OTHER INFORMATION: Fab dimer light chain
<220> FEATURE:
<221> NAME/KEY: regions CDR
<222> LOCATION: (1)..(234)
<223> OTHER INFORMATION: Xaa indicates CDR loops
<220> FEATURE:
<221> NAME/KEY: misc_feature
<222> LOCATION: (44)..(54)
<223> OTHER INFORMATION: Xaa can be any naturally occurring amino acid
<220> FEATURE:
<221> NAME/KEY: misc_feature
<222> LOCATION: (69)..(76)
<223> OTHER INFORMATION: Xaa can be any naturally occurring amino acid
<220> FEATURE:
<221> NAME/KEY: misc_feature
<222> LOCATION: (109)..(116)
<223> OTHER INFORMATION: Xaa can be any naturally occurring amino acid
```

<400> SEQUENCE: 19

Met Leu Gly Val Leu Val Leu Gly Ala Leu Ala Leu Ala Gly Leu Val
1               5                   10                  15

Phe Pro Glu Asp Ile Val Leu Thr Gln Ser Pro Ala Thr Leu Ser Leu
            20                  25                  30

Ser Pro Gly Glu Arg Ala Thr Leu Ser Cys Arg Xaa Xaa Xaa Xaa Xaa
        35                  40                  45

Xaa Xaa Xaa Xaa Xaa Xaa Trp Tyr Gln Gln Lys Pro Gly Gln Ala Pro
    50                  55                  60

Arg Leu Leu Ile Xaa Xaa Xaa Xaa Xaa Xaa Xaa Gly Val Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Thr Tyr Tyr Cys Xaa Xaa Xaa Xaa
            100                 105                 110

Xaa Xaa Xaa Xaa Thr Phe Gly Gln Gly Thr Lys Val Glu Ile Lys Arg
    115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Gly Thr Lys Ser Phe Asn Arg Gly Glu Cys
225                 230

<210> SEQ ID NO 20
<211> LENGTH: 376
<212> TYPE: PRT
<213> ORGANISM: artificial
<220> FEATURE:
<223> OTHER INFORMATION: Fab fusion protein, heavy chain and IgE CH4 domain
<220> FEATURE:
<221> NAME/KEY: regions CDR
<222> LOCATION: (1)..(376)
<223> OTHER INFORMATION: Xaa indicate CDR loops
<220> FEATURE:
<221> NAME/KEY: misc_feature
<222> LOCATION: (46)..(54)
<223> OTHER INFORMATION: Xaa can be any naturally occurring amino acid
<220> FEATURE:
<221> NAME/KEY: misc_feature
<222> LOCATION: (66)..(85)
<223> OTHER INFORMATION: Xaa can be any naturally occurring amino acid
<220> FEATURE:
<221> NAME/KEY: misc_feature
<222> LOCATION: (118)..(129)
<223> OTHER INFORMATION: Xaa can be any naturally occurring amino acid

<400> SEQUENCE: 20

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Glu Ser Leu Lys Ile Ser Cys Lys Gly Ser Gly Xaa Xaa Xaa
        35                  40                  45

Xaa Xaa Xaa Xaa Xaa Xaa Trp Val Arg Gln Met Pro Gly Lys Gly Leu
    50                  55                  60

Glu Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Xaa Xaa Xaa Xaa Xaa Xaa Xaa Xaa Xaa Xaa Xaa
        115                 120                 125

Xaa Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Asp Ser Glu Tyr Pro Pro Arg Ala Ala Pro
            260                 265                 270

```
Glu Val Tyr Ala Phe Ala Thr Pro Glu Trp Pro Gly Ser Arg Asp Lys
    275                 280                 285

Arg Thr Leu Ala Cys Leu Ile Gln Asn Phe Met Pro Glu Asp Ile Ser
    290                 295                 300

Val Gln Trp Leu His Asn Glu Val Gln Leu Pro Asp Ala Arg His Ser
305                 310                 315                 320

Thr Thr Gln Pro Arg Lys Thr Lys Gly Ser Gly Phe Phe Val Phe Ser
                325                 330                 335

Arg Leu Glu Val Thr Arg Ala Glu Trp Glu Gln Lys Asp Glu Phe Ile
            340                 345                 350

Cys Arg Ala Val His Glu Ala Ala Ser Pro Ser Gln Thr Val Gln Arg
        355                 360                 365

Ala Val Ser Val Asn Pro Gly Lys
    370                 375

<210> SEQ ID NO 21
<211> LENGTH: 705
<212> TYPE: DNA
<213> ORGANISM: artificial
<220> FEATURE:
<223> OTHER INFORMATION: Fab dimer light chain
<220> FEATURE:
<221> NAME/KEY: region CDR
<222> LOCATION: (1)..(705)
<223> OTHER INFORMATION: n is CDR loops
<220> FEATURE:
<221> NAME/KEY: misc_feature
<222> LOCATION: (130)..(162)
<223> OTHER INFORMATION: n is a, c, g, or t
<220> FEATURE:
<221> NAME/KEY: misc_feature
<222> LOCATION: (205)..(228)
<223> OTHER INFORMATION: n is a, c, g, or t
<220> FEATURE:
<221> NAME/KEY: misc_feature
<222> LOCATION: (325)..(348)
<223> OTHER INFORMATION: n is a, c, g, or t

<400> SEQUENCE: 21
atgcttgggg tcctggtcct tggcgcgctg gccctggcag gcctggtctt ccccgaggat      60
atcgtgctga cccagagccc ggcgaccctg agcctgtctc cgggcgaacg tgcgaccctg     120
agctgcagan nnnnnnnnn nnnnnnnnnn nnnnnnnnnn nntggtacca gcagaaacca     180
ggtcaagcac cgcgtctatt aattnnnnnn nnnnnnnnnn nnnnnnnngg ggtcccggcg     240
cgttttagcg gctctggatc cggcacggat tttaccctga ccattagcag cctggaacct     300
gaagactttg cgacttatta ttgcnnnnnn nnnnnnnnnn nnnnnnnnac ctttggccag     360
ggtacgaaag ttgaaattaa acgtacggtg gctgctccga gcgtgtttat ttttccgccg     420
agcgatgaac aactgaaaag cggcacggcg agcgtggtgt gcctgctgaa caacttttat     480
ccgcgtgaag cgaaagttca gtggaaagta gacaacgcgc tgcaaagcgg caacagccag     540
gaaagcgtga ccgaacagga tagcaaagat agcacctatt ctctgagcag cacccctgacc     600 ctgagcaaag cggattatga aaaacataaa gtgtatgcgt gcgaagtgac ccatcaaggt     660
ctgagcagcc cggggactaa atcttttaat cgtggcgagt gctga                    705

<210> SEQ ID NO 22
<211> LENGTH: 1131
<212> TYPE: DNA
<213> ORGANISM: artificial
<220> FEATURE:
<223> OTHER INFORMATION: Fab dimer heavy chain and IgE CH4 domain
<220> FEATURE:
<221> NAME/KEY: regions CDR
```

<222> LOCATION: (1)..(1131)
<223> OTHER INFORMATION: n stands for CDR loops
<220> FEATURE:
<221> NAME/KEY: misc_feature
<222> LOCATION: (136)..(162)
<223> OTHER INFORMATION: n is a, c, g, or t
<220> FEATURE:
<221> NAME/KEY: misc_feature
<222> LOCATION: (196)..(255)
<223> OTHER INFORMATION: n is a, c, g, or t
<220> FEATURE:
<221> NAME/KEY: misc_feature
<222> LOCATION: (352)..(387)
<223> OTHER INFORMATION: n is a, c, g, or t

<400> SEQUENCE: 22

```
atgaaacacc tgtggttctt cctcctgctg gtggcagctc ccagatgggt cctgtcccag      60
gtgcaattgg ttcagagcgg cgcggaagtg aaaaaaccgg gcgaaagcct gaaaattagc     120
tgcaaaggtt ccggannnnn nnnnnnnnnn nnnnnnnnnn nntgggtgcg ccagatgcct     180
gggaagggtc tcgagnnnnn nnnnnnnnnn nnnnnnnnnn nnnnnnnnnn nnnnnnnnnn     240
nnnnnnnnnn nnnnncaggt gaccattagc gcggataaaa gcattagcac cgcgtatctt     300
caatggagca gcctgaaagc gagcgatacg gccatgtatt attgcgcgcg tnnnnnnnnn     360
nnnnnnnnnn nnnnnnnnnn nnnnnntgg ggccaaggca ccctggtgac ggttagctca     420
gcgtcgacca aaggtccaag cgtgtttccg ctggctccga gcagcaaaag caccagcggc     480
ggcacggctg ccctgggctg cctggttaaa gattatttcc cggaaccagt caccgtgagc     540
tggaacagcg gggcgctgac cagcggcgtg cataccttc cggcggtgct gcaaagcagc     600
ggcctgtata gcctgagcag cgttgtgacc gtgccgagca gcagcttagg cactcagacc     660
tatatttgca acgtgaacca taaaccgagc aacaccaaag tggataaaaa agtggaaccg     720
aaaagctgcg ataaaactca cacatgtcca ccgtgcccag cacctgaact cctgggggga     780
ccgtcagaca cgcgagtaccc cccgcgtgct gccccggaag tctatgcgtt tgcgacgccg     840
gagtggccgg ggagtcggga caagcgcacc ctcgcctgcc tgatccagaa cttcatgcct     900
gaggacatct cggtgcagtg gctacacaac gaggtgcagc tccccgacgc ccggcacagc     960
acgacgcagc cccgcaagac caagggctcc ggcttcttcg tcttcagccg cctggaggtg    1020
accagggccg aatgggagca gaaagatgag ttcatctgcc gtgcagtcca tgaggcagcg    1080
agcccctcac agaccgtcca gcgagcggtg tctgtaaatc ccggtaaata g             1131
```

<210> SEQ ID NO 23
<211> LENGTH: 15
<212> TYPE: PRT
<213> ORGANISM: artificial
<220> FEATURE:
<223> OTHER INFORMATION: epitope tag 1

<400> SEQUENCE: 23

Gly Ala Pro Val Pro Tyr Pro Asp Pro Leu Glu Pro Arg Ala Ala
1               5                   10                  15

<210> SEQ ID NO 24
<211> LENGTH: 8
<212> TYPE: PRT
<213> ORGANISM: artificial
<220> FEATURE:
<223> OTHER INFORMATION: epitope tag 2

<400> SEQUENCE: 24

Glu Ser Ser Glu Glu Gly Gly Cys
1               5

```
<210> SEQ ID NO 25
<211> LENGTH: 446
<212> TYPE: PRT
<213> ORGANISM: homo sapien
<220> FEATURE:
<221> NAME/KEY: misc_feature
<222> LOCATION: (1)..(118)
<223> OTHER INFORMATION: Xaa can be any naturally occurring amino acid
<220> FEATURE:
<221> NAME/KEY: heavy constant region of EU IgG1
<222> LOCATION: (119)..(446)
<223> OTHER INFORMATION: Xaa represent the light variable region

<400> SEQUENCE: 25

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Gln
            260                 265                 270

Val Lys Phe Asn Trp Tyr Val Asp Gly Val Gln Val His Asn Ala Lys
        275                 280                 285

Thr Lys Pro Arg Glu Gln Gln Tyr Asp Ser Thr Tyr Arg Val Val Ser
290                 295                 300

Val Leu Thr Val Leu His Gln Asn Trp Leu Asp Gly Lys Glu Tyr Lys
305                 310                 315                 320

Cys Lys Val Ser Asn Lys Ala Leu Pro Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Arg Asp Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Asp Gly Glu Pro Glu Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 26
<211> LENGTH: 8
<212> TYPE: PRT
<213> ORGANISM: artificial
<220> FEATURE:
<223> OTHER INFORMATION: M2" IgE splice variant 1

<400> SEQUENCE: 26

Glu Ser Ser Glu Glu Gly Gly Cys
1               5

<210> SEQ ID NO 27
<211> LENGTH: 8
<212> TYPE: PRT
<213> ORGANISM: artificial
<220> FEATURE:
<223> OTHER INFORMATION: M2" IgE CH4 splice variant 2

<400> SEQUENCE: 27

Glu Ser Ser Arg Arg Gly Gly Cys
1               5

<210> SEQ ID NO 28
<211> LENGTH: 8
<212> TYPE: PRT
<213> ORGANISM: artificial
<220> FEATURE:
<223> OTHER INFORMATION: M2" IgE CH4 splice variant 3

<400> SEQUENCE: 28

Glu Ser Ser Lys Lys Gly Gly Cys
1               5

<210> SEQ ID NO 29
<211> LENGTH: 8
<212> TYPE: PRT
<213> ORGANISM: artificial
<220> FEATURE:
<223> OTHER INFORMATION: M2" IgE CH4 splice variant 4

<400> SEQUENCE: 29

Glu Ser Ser Cys Arg Gly Gly Cys
1               5

<210> SEQ ID NO 30
<211> LENGTH: 8
<212> TYPE: PRT
<213> ORGANISM: artificial
<220> FEATURE:
<223> OTHER INFORMATION: M2" CH4 splice variant 5
```

<400> SEQUENCE: 30

Glu Ser Ser Arg Cys Gly Gly Cys
1               5

<210> SEQ ID NO 31
<211> LENGTH: 33
<212> TYPE: DNA
<213> ORGANISM: artificial
<220> FEATURE:
<223> OTHER INFORMATION: ATG47 forward primer

<400> SEQUENCE: 31
ctcacacatg tccaccgtgc ccagcacctg aac                                    33

<210> SEQ ID NO 32
<211> LENGTH: 39
<212> TYPE: DNA
<213> ORGANISM: artificial
<220> FEATURE:
<223> OTHER INFORMATION: ATG46 reverse primer

<400> SEQUENCE: 32
tgtggccggc cctatttacc gggatttaca gacaccgct                              39

<210> SEQ ID NO 33
<211> LENGTH: 26
<212> TYPE: DNA
<213> ORGANISM: artificial
<220> FEATURE:
<223> OTHER INFORMATION: ATG51 forward primer

<400> SEQUENCE: 33
gttgaaatta aacgtacggt ggctgc                                            26

<210> SEQ ID NO 34
<211> LENGTH: 48
<212> TYPE: DNA
<213> ORGANISM: artificial
<220> FEATURE:
<223> OTHER INFORMATION: ATG56 reverse primer

<400> SEQUENCE: 34
ggacatgtgt gagttttatc gcagcttttc ggttccactt ttttatcc                    48

<210> SEQ ID NO 35
<211> LENGTH: 22
<212> TYPE: DNA
<213> ORGANISM: artificial
<220> FEATURE:
<223> OTHER INFORMATION: ATG75 forward primer

<400> SEQUENCE: 35
caggtgcaat tggttcagag cg                                                22

<210> SEQ ID NO 36
<211> LENGTH: 38
<212> TYPE: DNA
<213> ORGANISM: artificial
<220> FEATURE:
<223> OTHER INFORMATION: ATG76 reverse primer

<400> SEQUENCE: 36
cgactcccgg gttactattt accgggattt acagacac                               38

<210> SEQ ID NO 37

```
<211> LENGTH: 35
<212> TYPE: DNA
<213> ORGANISM: artificial
<220> FEATURE:
<223> OTHER INFORMATION: ATG85 forward primer

<400> SEQUENCE: 37
gggggaccgt caaaaagcaa atacccgccg cgtgc                              35

<210> SEQ ID NO 38
<211> LENGTH: 35
<212> TYPE: DNA
<213> ORGANISM: artificial
<220> FEATURE:
<223> OTHER INFORMATION: ATG86 reverse primer

<400> SEQUENCE: 38
gcacgcggcg ggtatttgct ttttgacggt ccccc                              35

<210> SEQ ID NO 39
<211> LENGTH: 100
<212> TYPE: DNA
<213> ORGANISM: artificial
<220> FEATURE:
<223> OTHER INFORMATION: ATG105 forward primer

<400> SEQUENCE: 39
gcgcggccgc gccaccatga acacctgtg gttcttcctc ctgctggtgg cagctcccag    60
atgggtcctg tcccaggtgc aattggttca gagcggcgcg                        100

<210> SEQ ID NO 40
<211> LENGTH: 20
<212> TYPE: DNA
<213> ORGANISM: artificial
<220> FEATURE:
<223> OTHER INFORMATION: ATG106 reverse primer

<400> SEQUENCE: 40
cctttggtcg acgctgagct                                               20

<210> SEQ ID NO 41
<211> LENGTH: 417
<212> TYPE: DNA
<213> ORGANISM: artificial
<220> FEATURE:
<223> OTHER INFORMATION: heavy chain variable region of AB25
<220> FEATURE:
<221> NAME/KEY: misc_feature
<222> LOCATION: (133)..(162)
<223> OTHER INFORMATION: n is a, c, g, or t
<220> FEATURE:
<221> NAME/KEY: misc_feature
<222> LOCATION: (196)..(255)
<223> OTHER INFORMATION: n is a, c, g, or t
<220> FEATURE:
<221> NAME/KEY: misc_feature
<222> LOCATION: (352)..(384)
<223> OTHER INFORMATION: n is a, c, g, or t

<400> SEQUENCE: 41
atgaaacacc tgtggttctt cctcctgctg gtggcagctc ccagatgggt cctgtcccag    60
gtgcaattgg ttcagagcgg cgcggaagtg aaaaaaccgg cgcgagcgt gaaagtgagc    120 tgcaaagcct ccnnnnnnnn nnnnnnnnnn nnnnnnnnnn nntgggtccg ccaagcccct    180
gggcagggtc tcgagnnnnn nnnnnnnnnn nnnnnnnnnn nnnnnnnnnn nnnnnnnnnn    240
nnnnnnnnnn nnnncgggt gaccatgacc cgtgatacca gcattagcac cgcgtatatg    300
```

```
gaactgagca gcctgcgtag cgaagatacg gccgtgtatt attgcgcgcg tnnnnnnnnn      360
nnnnnnnnnn nnnnnnnnnn nnnntggggc caaggcaccc tggtgacggt tagctca         417
```

<210> SEQ ID NO 42
<211> LENGTH: 139
<212> TYPE: PRT
<213> ORGANISM: artificial
<220> FEATURE:
<223> OTHER INFORMATION: heavy chain variable region of AB25, amino acid
      sequence
<220> FEATURE:
<221> NAME/KEY: misc_feature
<222> LOCATION: (45)..(54)
<223> OTHER INFORMATION: Xaa can be any naturally occurring amino acid
<220> FEATURE:
<221> NAME/KEY: misc_feature
<222> LOCATION: (66)..(85)
<223> OTHER INFORMATION: Xaa can be any naturally occurring amino acid
<220> FEATURE:
<221> NAME/KEY: misc_feature
<222> LOCATION: (118)..(128)
<223> OTHER INFORMATION: Xaa can be any naturally occurring amino acid

<400> SEQUENCE: 42

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Xaa Xaa Xaa Xaa
        35                  40                  45

Xaa Xaa Xaa Xaa Xaa Xaa Trp Val Arg Gln Ala Pro Gly Gln Gly Leu
    50                  55                  60

Glu Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Arg Val Thr Met Thr Arg Asp Thr Ser Ile Ser
                85                  90                  95

Thr Ala Tyr Met Glu Leu Ser Ser Leu Arg Ser Glu Asp Thr Ala Val
            100                 105                 110

Tyr Tyr Cys Ala Arg Xaa Xaa Xaa Xaa Xaa Xaa Xaa Xaa Xaa Xaa Xaa
        115                 120                 125

Trp Gly Gln Gly Thr Leu Val Thr Val Ser Ser
    130                 135
```

<210> SEQ ID NO 43
<211> LENGTH: 390
<212> TYPE: DNA
<213> ORGANISM: artificial
<220> FEATURE:
<223> OTHER INFORMATION: light chain variable region of AB25
<220> FEATURE:
<221> NAME/KEY: misc_feature
<222> LOCATION: (130)..(165)
<223> OTHER INFORMATION: n is a, c, g, or t
<220> FEATURE:
<221> NAME/KEY: misc_feature
<222> LOCATION: (208)..(231)
<223> OTHER INFORMATION: n is a, c, g, or t
<220> FEATURE:
<221> NAME/KEY: misc_feature
<222> LOCATION: (328)..(351)
<223> OTHER INFORMATION: n is a, c, g, or t

<400> SEQUENCE: 43

```
atggtgttgc agacccaggt cttcatttct ctgttgctct ggatctctgg tgcctacggg      60
gatatcgtgc tgacccagag cccggcgacc ctgagcctgt ctccgggcga acgtgcgacc     120
```

```
ctgagctgcn nnnnnnnnnn nnnnnnnnnn nnnnnnnnnn nnnnntggta ccagcagaaa      180
ccaggtcaag caccgcgtct attaattnnn nnnnnnnnnn nnnnnnnnnn nggggtcccg      240
gcgcgtttta gcggctctgg atccggcacg gattttaccc tgaccattag cagcctggaa      300
cctgaagact ttgcggttta ttattgcnnn nnnnnnnnnn nnnnnnnnnn nacctttggc      360
cagggtacga agttgaaat taaacgtacg                                       390
```

```
<210> SEQ ID NO 44
<211> LENGTH: 130
<212> TYPE: PRT
<213> ORGANISM: artificial
<220> FEATURE:
<223> OTHER INFORMATION: light chain variable region of AB25, amino acid
      sequence
<220> FEATURE:
<221> NAME/KEY: misc_feature
<222> LOCATION: (44)..(55)
<223> OTHER INFORMATION: Xaa can be any naturally occurring amino acid
<220> FEATURE:
<221> NAME/KEY: misc_feature
<222> LOCATION: (70)..(77)
<223> OTHER INFORMATION: Xaa can be any naturally occurring amino acid
<220> FEATURE:
<221> NAME/KEY: misc_feature
<222> LOCATION: (110)..(117)
<223> OTHER INFORMATION: Xaa can be any naturally occurring amino acid
```

<400> SEQUENCE: 44

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Xaa Xaa Xaa Xaa Xaa
        35                  40                  45

Xaa Xaa Xaa Xaa Xaa Xaa Xaa Trp Tyr Gln Gln Lys Pro Gly Gln Ala
    50                  55                  60

Pro Arg Leu Leu Ile Xaa Xaa Xaa Xaa Xaa Xaa Xaa Xaa Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Xaa Xaa Xaa
            100                 105                 110

Xaa Xaa Xaa Xaa Xaa Thr Phe Gly Gln Gly Thr Lys Val Glu Ile Lys
        115                 120                 125

Arg Thr
    130

```
<210> SEQ ID NO 45
<211> LENGTH: 427
<212> TYPE: PRT
<213> ORGANISM: homo sapien
```

<400> SEQUENCE: 45

Ser Thr Gln Ser Pro Ser Val Phe Pro Leu Thr Arg Cys Cys Lys Asn
1               5                   10                  15

Ile Pro Ser Asn Ala Thr Ser Val Thr Leu Gly Cys Leu Ala Thr Gly
            20                  25                  30

Tyr Phe Pro Glu Pro Val Met Val Thr Trp Asp Thr Gly Ser Leu Asn
        35                  40                  45

Gly Thr Thr Met Thr Leu Pro Ala Thr Thr Leu Thr Leu Ser Gly His
    50                  55                  60

```
Tyr Ala Thr Ile Ser Leu Leu Thr Val Ser Gly Ala Trp Ala Lys Gln
 65                  70                  75                  80

Met Phe Thr Cys Arg Val Ala His Thr Pro Ser Ser Thr Asp Trp Val
                 85                  90                  95

Asp Asn Lys Thr Phe Ser Val Cys Ser Arg Asp Phe Thr Pro Pro Thr
            100                 105                 110

Val Lys Ile Leu Gln Ser Ser Cys Asp Gly Gly His Phe Pro Pro
        115                 120                 125

Thr Ile Gln Leu Leu Cys Leu Val Ser Gly Tyr Thr Pro Gly Thr Ile
130                 135                 140

Asn Ile Thr Trp Leu Glu Asp Gly Gln Val Met Asp Val Asp Leu Ser
145                 150                 155                 160

Thr Ala Ser Thr Gln Glu Gly Glu Leu Ala Ser Thr Gln Ser Glu
                165                 170                 175

Leu Thr Leu Ser Gln Lys His Trp Leu Ser Asp Arg Thr Tyr Thr Cys
                180                 185                 190

Gln Val Thr Tyr Gln Gly His Thr Phe Glu Asp Ser Thr Lys Lys Cys
            195                 200                 205

Ala Asp Ser Asn Pro Arg Gly Val Ser Ala Tyr Leu Ser Arg Pro Ser
210                 215                 220

Pro Phe Asp Leu Phe Ile Arg Lys Ser Pro Thr Ile Thr Cys Leu Val
225                 230                 235                 240

Val Asp Leu Ala Pro Ser Lys Gly Thr Val Asn Leu Thr Trp Ser Arg
                245                 250                 255

Ala Ser Gly Lys Pro Val Asn His Ser Thr Arg Lys Glu Glu Lys Gln
            260                 265                 270

Arg Asn Gly Thr Leu Thr Val Thr Ser Thr Leu Pro Val Gly Thr Arg
            275                 280                 285

Asp Trp Ile Glu Gly Glu Thr Tyr Gln Cys Arg Val Thr His Pro His
        290                 295                 300

Leu Pro Arg Ala Leu Met Arg Ser Thr Thr Lys Thr Ser Gly Pro Arg
305                 310                 315                 320

Ala Ala Pro Glu Val Tyr Ala Phe Ala Thr Pro Glu Trp Pro Gly Ser
                325                 330                 335

Arg Asp Lys Arg Thr Leu Ala Cys Leu Ile Gln Asn Phe Met Pro Glu
            340                 345                 350

Asp Ile Ser Val Gln Trp Leu His Asn Glu Val Gln Leu Pro Asp Ala
        355                 360                 365

Arg His Ser Thr Thr Gln Pro Arg Lys Thr Lys Gly Ser Gly Phe Phe
370                 375                 380

Val Phe Ser Arg Leu Glu Val Thr Arg Ala Glu Trp Glu Gln Lys Asp
385                 390                 395                 400

Glu Phe Ile Cys Arg Ala Val His Glu Ala Ser Pro Ser Gln Thr
                405                 410                 415

Val Gln Arg Ala Val Ser Val Asn Pro Gly Lys
            420                 425

<210> SEQ ID NO 46
<211> LENGTH: 4
<212> TYPE: PRT
<213> ORGANISM: artificial
<220> FEATURE:
<223> OTHER INFORMATION: tetrapeptide

<400> SEQUENCE: 46

Val Phe Leu Phe
```

```
<210> SEQ ID NO 47
<211> LENGTH: 4
<212> TYPE: PRT
<213> ORGANISM: artificial
<220> FEATURE:
<223> OTHER INFORMATION: tetrapeptide

<400> SEQUENCE: 47

Asp Ser Glu Tyr
1

<210> SEQ ID NO 48
<211> LENGTH: 4
<212> TYPE: PRT
<213> ORGANISM: artificial
<220> FEATURE:
<223> OTHER INFORMATION: tetrapeptide

<400> SEQUENCE: 48

Lys Ser Lys Tyr
1

<210> SEQ ID NO 49
<211> LENGTH: 4
<212> TYPE: PRT
<213> ORGANISM: artificial
<220> FEATURE:
<223> OTHER INFORMATION: tetrapeptide

<400> SEQUENCE: 49

Asp Glu Glu Tyr
1

<210> SEQ ID NO 50
<211> LENGTH: 4
<212> TYPE: PRT
<213> ORGANISM: artificial
<220> FEATURE:
<223> OTHER INFORMATION: tetrapeptide

<400> SEQUENCE: 50

Lys Arg Lys Tyr
1

<210> SEQ ID NO 51
<211> LENGTH: 4
<212> TYPE: PRT
<213> ORGANISM: artificial
<220> FEATURE:
<223> OTHER INFORMATION: tetrapeptide

<400> SEQUENCE: 51

Ser Glu Ser Glu
1

<210> SEQ ID NO 52
<211> LENGTH: 4
<212> TYPE: PRT
<213> ORGANISM: artificial
<220> FEATURE:
<223> OTHER INFORMATION: tetrapeptide

<400> SEQUENCE: 52

Ser Asp Ser Asp
1
```

```
<210> SEQ ID NO 53
<211> LENGTH: 4
<212> TYPE: PRT
<213> ORGANISM: artificial
<220> FEATURE:
<223> OTHER INFORMATION: tetrapeptide

<400> SEQUENCE: 53

Ser Lys Ser Lys
1

<210> SEQ ID NO 54
<211> LENGTH: 4
<212> TYPE: PRT
<213> ORGANISM: artificial
<220> FEATURE:
<223> OTHER INFORMATION: tetrapeptide

<400> SEQUENCE: 54

Ser Glu Ser Tyr
1

<210> SEQ ID NO 55
<211> LENGTH: 4
<212> TYPE: PRT
<213> ORGANISM: artificial
<220> FEATURE:
<223> OTHER INFORMATION: tetrapeptide

<400> SEQUENCE: 55

Ser Glu Ser Tyr
1

<210> SEQ ID NO 56
<211> LENGTH: 4
<212> TYPE: PRT
<213> ORGANISM: artificial
<220> FEATURE:
<223> OTHER INFORMATION: tetrapeptide

<400> SEQUENCE: 56

Ser Asp Ser Tyr
1

<210> SEQ ID NO 57
<211> LENGTH: 4
<212> TYPE: PRT
<213> ORGANISM: artificial
<220> FEATURE:
<223> OTHER INFORMATION: tetrapeptide

<400> SEQUENCE: 57

Ser Lys Ser Tyr
1

<210> SEQ ID NO 58
<211> LENGTH: 4
<212> TYPE: PRT
<213> ORGANISM: artificial
<220> FEATURE:
<223> OTHER INFORMATION: tetrapeptide

<400> SEQUENCE: 58

Ser Arg Ser Tyr
1

<210> SEQ ID NO 59
```

```
<211> LENGTH: 4
<212> TYPE: PRT
<213> ORGANISM: artificial
<220> FEATURE:
<223> OTHER INFORMATION: tetrapeptide

<400> SEQUENCE: 59

Asp Asp Asp Tyr
1

<210> SEQ ID NO 60
<211> LENGTH: 4
<212> TYPE: PRT
<213> ORGANISM: artificial
<220> FEATURE:
<223> OTHER INFORMATION: tetrapeptide

<400> SEQUENCE: 60

Asp Asp Glu Tyr
1

<210> SEQ ID NO 61
<211> LENGTH: 4
<212> TYPE: PRT
<213> ORGANISM: artificial
<220> FEATURE:
<223> OTHER INFORMATION: tetrapeptide

<400> SEQUENCE: 61

Asp Glu Asp Tyr
1

<210> SEQ ID NO 62
<211> LENGTH: 4
<212> TYPE: PRT
<213> ORGANISM: artificial
<220> FEATURE:
<223> OTHER INFORMATION: tetrapeptide

<400> SEQUENCE: 62

Glu Glu Glu Tyr
1

<210> SEQ ID NO 63
<211> LENGTH: 4
<212> TYPE: PRT
<213> ORGANISM: artificial
<220> FEATURE:
<223> OTHER INFORMATION: tetrapeptide

<400> SEQUENCE: 63

Glu Asp Asp Tyr
1

<210> SEQ ID NO 64
<211> LENGTH: 4
<212> TYPE: PRT
<213> ORGANISM: artificial
<220> FEATURE:
<223> OTHER INFORMATION: tetrapeptide

<400> SEQUENCE: 64

Glu Asp Glu Tyr
1

<210> SEQ ID NO 65
<211> LENGTH: 4
<212> TYPE: PRT
```

```
<213> ORGANISM: artificial
<220> FEATURE:
<223> OTHER INFORMATION: tetrapeptide

<400> SEQUENCE: 65

Glu Glu Asp Tyr
1

<210> SEQ ID NO 66
<211> LENGTH: 4
<212> TYPE: PRT
<213> ORGANISM: artificial
<220> FEATURE:
<223> OTHER INFORMATION: tetrapeptide

<400> SEQUENCE: 66

Arg Arg Arg Tyr
1

<210> SEQ ID NO 67
<211> LENGTH: 4
<212> TYPE: PRT
<213> ORGANISM: artificial
<220> FEATURE:
<223> OTHER INFORMATION: tetrapeptide

<400> SEQUENCE: 67

Arg Lys Arg Tyr
1

<210> SEQ ID NO 68
<211> LENGTH: 4
<212> TYPE: PRT
<213> ORGANISM: artificial
<220> FEATURE:
<223> OTHER INFORMATION: tetrapeptide

<400> SEQUENCE: 68

Arg Arg Lys Tyr
1

<210> SEQ ID NO 69
<211> LENGTH: 4
<212> TYPE: PRT
<213> ORGANISM: artificial
<220> FEATURE:
<223> OTHER INFORMATION: tetrapeptide

<400> SEQUENCE: 69

Arg Lys Lys Tyr
1

<210> SEQ ID NO 70
<211> LENGTH: 4
<212> TYPE: PRT
<213> ORGANISM: artificial
<220> FEATURE:
<223> OTHER INFORMATION: tetrapeptide

<400> SEQUENCE: 70

Lys Lys Lys Tyr
1

<210> SEQ ID NO 71
<211> LENGTH: 4
<212> TYPE: PRT
<213> ORGANISM: artificial
<220> FEATURE:
```

```
<223> OTHER INFORMATION: tetrapeptide

<400> SEQUENCE: 71

Lys Arg Arg Tyr
1

<210> SEQ ID NO 72
<211> LENGTH: 4
<212> TYPE: PRT
<213> ORGANISM: artificial
<220> FEATURE:
<223> OTHER INFORMATION: tetrapeptide

<400> SEQUENCE: 72

Lys Lys Arg Tyr
1

<210> SEQ ID NO 73
<211> LENGTH: 5
<212> TYPE: PRT
<213> ORGANISM: artificial
<220> FEATURE:
<223> OTHER INFORMATION: linker

<400> SEQUENCE: 73

Gly Gly Gly Gly Ser
1               5
```

DIMERIC MOLECULAR COMPLEXES

RELATED APPLICATIONS/PATENTS AND INCORPORATION BY REFERENCE

This application is a National Stage Application filed under 35 U.S.C. §371 based on International Application No. PCT/EP2007/004601, filed May 24, 2007, which claims the benefit of U.S. Provisional Patent Application No. 60/808,840, filed May 25, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

SUMMARY OF THE INVENTION

The present invention provides dimeric molecular complexes comprising a first and second fusion protein, wherein each fusion protein comprises from its N to C terminus (a) a biological effector moiety, (b) a hinge region of an IgG molecule bound to the biological effector moiety and (c) a CH4 dimerization domain of an IgE molecule covalently bound to the hinge region, wherein the molecular complex comprises a disulfide bond between a cysteine residue in the hinge region of the first fusion protein and a cysteine residue in the hinge region of the second fusion protein.

Preferred biological effector moieties are a single chain antibody, an Fab fragment, an extracellular domain of a type I membrane receptor, a cytokine, a chemokine, an enzyme, a toxin or a detectable marker. More preferred biological effector moieties are a single chain antibody, an Fab fragment, a toxin or a detectable marker.

In one embodiment, the dimeric molecular complex of the invention comprises two fusion proteins each comprising identical biological effector moieties. In another embodiment, the two fusion proteins within the complex each comprise different biological effector moieties. In a preferred embodiment, the biological effector moieties are antigen binding sites, with either the same or different binding specificities.

Each fusion protein comprises a hinge region comprising an amino acid residues 223 to 243 of SEQ ID NO:25, wherein positions 240-243 are occupied by the tetrapeptide VFLF. In preferred embodiments, the tetrapeptide VFLF (SEQ ID NO:46) is replaced with a tetrapeptide selected from the group consisting of DSEY (SEQ ID NO:47), KSKY (SEQ ID NO:48), DEEY (SEQ ID NO:49) and KRKY (SEQ ID NO:50). Most preferred are embodiments where the tetrapeptide is DSEY (SEQ ID NO:47) or KSKY (SEQ ID NO:48).

In another aspect, the invention provides dimeric molecular complexes comprising a first and second fusion protein, wherein each fusion protein comprises from its N to C terminus (a) a CH4 dimerization domain of an M2" IgE splice variant, (b) an amino acid linker which is covalently bound to the CH4 dimerization domain and (c) an extracellular domain of a type II membrane receptor, wherein the molecular complex comprises a disulfide bond between cysteine residues within the C terminal M2" IgE splice variant CH4 dimerization domains of each of the two fusion proteins. In a preferred embodiment, the M2" IgE splice variant is SEQ ID NO:26, SEQ ID NO: 27, SEQ ID NO: 28, SEQ ID NO:29 or SEQ ID NO:30. In one embodiment, the type II membrane receptor is a myeloid DAP12-associating lectin-1 (MDL-1) receptor.

In another aspect, the invention provides nucleic acid molecules which encode the fusion proteins which comprise the dimeric molecular complexes. In one embodiment, a nucleic acid molecule encodes the fusion protein of SEQ ID NO:1.

In another aspect, the invention provides pharmaceutical compositions including the subject dimeric molecular complexes.

In another aspect, the invention relates to a method of treatment using the subject dimeric molecular complexes. In preferred embodiments, methods of treatment involve administration of dimeric molecular complexes comprised of fusion proteins as described above, conjugated to chemotherapeutic agents or to toxins. In a preferred embodiment, the biological effector moiety of at least one of the two fusion proteins comprises an antigen binding site.

In another aspect, the invention relates to a method of imaging a target area of the body using a dimeric molecular complex of the invention comprised of two fusion proteins, wherein the biological effector moiety of the first fusion protein comprises an antigen binding site and the biological effector moiety of the second fusion protein comprises a detectable signal.

BRIEF DESCRIPTION OF THE FIGURES

FIGS. 1A-D. Schematic drawings of various dimeric molecular complexes. In each case, disulfide bonds are formed between the cysteines in the hinge region of the fusion proteins comprising the complex. FIG. 1A, a dimeric molecular complex in which the biological effector moiety is a single chain antibody. FIG. 1B, two monospecific dimeric molecular complexes in which the biological effector moiety is a Fab fragment; the complexes differ from each other in the sequence used to replace the "wild-type" tetrapeptide VFLF) within the hinge. FIG. 1C, a bispecific dimeric molecular complex in which the biological effector moieties are two different Fab fragments and the where each fusion protein further comprises a different M2" IgE splice variant at its C terminus (SEQ ID NOS:26 and 27). FIG. 1D, a dimeric molecular complex in which the biological effector moiety is an extracellular domain of a type I membrane receptor.

FIG. 3. Schematic showing generation of the single chain antibody 19G9scFv. The VH and VL regions were amplified by PCR using primers which introduced restriction sites and sites for overlap extension of the GGGGSGGGGSGGGGSGGGGS linker (SEQ ID NO:8). Following 15 cycles of extension, the scFv was amplified with the original forward and back primers shown for 35 cycles and then cloned by restriction digestion into the pz613 bacterial expression vector. VH forward primer, SEQ ID NO:15; VH back primer, SEQ ID NO:16; VL forward primer, SEQ ID NO:17; VL back primer, SEQ ID NO:18.

FIG. 4A, construction of an IgE CH4 dimerization domain fused to an IgG1 hinge. ATG001 primer, SEQ ID NO:9; ATG003 primer, SEQ ID NO:11; ATG004 primer, SEQ ID NO:12; ATG006 primer, SEQ ID NO:13. FIG. 4B, construction of an IgE CH4 dimerization domain fused to an IgG hinge with four amino acids mutated to create a more hydrophilic hinge (ATG019 primer, SEQ ID NO:14). Insert shows the sequence around the site of mutation including both the amino acid sequence, amino acids 252-281 of SEQ ID NO:1 and nucleotide sequence (nucleotides 783-869 of SEQ ID NO:2).

FIGS. 5A-B. Sequences of two 19G9scFv fusion proteins. FIG. 5A, amino acid sequence at bottom (SEQ ID NO:3) and nucleic acid sequence at top (SEQ ID NO:4) of "wild-type" 19G9scFv fusion protein contains the regions VH, bold italic; scFv linker, bold italic underline; VL and C-terminal extension, bold; IgG hinge, italic, with "wild-type" tetrapeptide in bold underline; IgE CH4, plain; C-terminal epitope tag, italic underline. FIG. 5B, amino acid sequence at bottom (SEQ ID NO:1) and nucleic acid sequence at top (SEQ ID NO:2) of "mutant" 19G9scFv fusion protein contains the regions VH, bold italic; scFv linker, bold italic underline; VL and C-terminal extension, bold; IgG hinge, italic, with hydrophilic tetrapeptide substitution in bold underline; IgE CH4, plain; C-terminal epitope tag, italic underline.

FIG. 6A-B. Characterization of a purified dimeric molecular complex comprising two fusion proteins containing the single chain antibody, 19G9scFv (sometimes referred to as 19G9scFv dimeric molecular complex). FIG. 6A, size exclusion chromatography (SEC) profile, which indicates pure protein is mainly a dimer (~90 kDa based on elution times of molecular weight standards). FIG. 6B, SDS-PAGE analysis of non-reduced 19G9scFv fusion protein (lanes 2 and 3, containing 2 μL and 5 μL of protein, respectively) and reduced 19G9scFv fusion protein (lanes 5 and 6, containing 2 μL and 5 μL of protein, respectively) is consistent with the calculated molecular weight of the dimeric complex (85.4 kDa) and of the 19G9scFv fusion protein monomer (42.7 kDa). Lanes 1 and 7 contain molecular weight markers.

DETAILED DESCRIPTION OF THE INVENTION

The invention exploits the self-dimerization properties of the IgE CH4 domain to provide dimeric molecular complexes comprising biological effector moieties. A "biological effector moiety" is a polypeptide which comprises the biologically active portion of molecules such as antibodies, type I and type II membrane receptors, cytokines, enzymes, and the like. Useful biological effector moieties include single chain antibodies, Fab fragments, extracellular domains of type I or type II membrane receptors, cytokines (including chemokines), active site domains of enzymes, protein hormones and peptide effector molecules.

The biological effector moieties in each of the two fusion proteins which comprise a dimeric molecular complex can be identical or can be moieties with two different functions (e.g., an antigen binding site and a toxin). Biological effector moieties which have a useful therapeutic or tissue specific targeting function are especially useful.

Dimeric molecular complexes are stable in vivo and bind to a target of interest with an affinity similar to that of the native molecule from which the biological effector moiety is derived.

Dimeric molecular complexes of the invention comprise two fusion proteins. In some embodiments, each fusion protein comprises the following, from N to C terminus: (a) a biological effector moiety, (b) a hinge region of an IgG molecule bound to the biological effector moiety; and (c) an IgE CH4 dimerization domain covalently bound to the hinge region. Dimerization of the CH4 dimerization domains of the first and second fusion proteins occurs by formation of disulfide bonds between cysteines in the hinge region of each fusion protein. See FIGS. 1A-D.

The effector molecule can be covalently attached directly to the native sequence of the $IgG_1$ hinge. In other embodiments, an amino acid linker can be employed. In such embodiments, the effector molecule is covalently attached to the linker, which is covalently bound to the $IgG_1$ hinge. The IgG hinge is preferably an $IgG_1$ hinge, preferably derived from human $IgG_1$, although hinge regions of $IgG_1$ from other species can be used (e.g., mouse, rabbit, etc.). In other embodiments, hinge regions from other IgGs may be used (e.g., $IgG_2$, $IgG_3$ and $IgG_4$).

The $IgG_1$ hinge, as used herein, comprises amino acid residues 223 to 243 from within the first beta strand of the $IgG_1$ CH2 domain, where the numbering is based on the sequence of the Eu $IgG_1$ heavy chain (SEQ ID NO:25) as described in Edelman et al. (1969) *Proc. Natl. Acad. Science USA,* 63, pp. 78-85. This sequence contains a hydrophobic tetrapeptide, VFLF at positions 240-243 (corresponding to positions 277-280 in SEQ ID NO:3). In a preferred embodiment, this hydrophobic tetrapeptide is replaced by a tetrapeptide of hydrophilic amino acids, Asp, Ser, Glu, and Tyr (DSEY) (amino acid residues 277-280 in SEQ ID NO:1), to increase solubility. The hinge and N-terminal CH2 sequences of $IgG_2$, $IgG_3$ or $IgG_4$ also contain the VFLF tetrapeptide and therefore hinge regions from these immunoglobulin molecules provide the same opportunities for substitution at these positions.

In another embodiment, modifications can be made in the hinge region to increase the ability to conjugate various molecules to the dimeric molecular complex. While lysine residues already present in the dimer can be used for conjugation, additional sites for conjugation can be provided by altering the same hydrophobic tetrapeptide (i.e. VFLF, at positions 277-280 in SEQ ID NO:3) that was changed to DSEY (resulting in SEQ ID NO:1) to, for example, the tetrapeptide, KSKY. The additional lysine residues provided by this substitution can be used to add polyglycols (e.g., PEG, POG) to a dimerized molecule to improve clearance. Alternatively, molecules such as toxins, detectable labels, radioactive molecules, etc., can be conjugated to fusion proteins of the dimeric molecular complex through these lysine residues. Methods of conjugation are well known in the art.

Dimeric Molecular Complexes Using Antibodies as Biological Effector Moieties scFv and Fab Dimers The dimeric molecular complexes of the invention can be formed using fusion proteins comprising antibodies as the biological effector moieties. In some embodiments, the biological effector moieties of each fusion protein are comprised of antigen binding sites. The antigen binding sites can be provided, for example, by a single-chain antibody (scFv) or an Fab fragment. The resulting dimeric molecular complex will comprise two antigen binding sites, which can be of the same or different specificities (i.e. forming monospecific or bispecific dimeric molecular complexes, respectively).

A monospecific dimeric molecular complex in which the biological effector moiety on both fusion proteins is a single chain antibody is shown schematically in FIG. 1A. FIG. 1B is a schematic representation of monospecific dimeric molecular complexes in which the biological effector moiety on each fusion protein is a Fab fragment (i.e. "Fab dimer"). FIG. 1C is a schematic representation of a bispecific dimeric molecular complex in which the biological effector moieties on the fusion proteins are Fab fragments with differing specificities.

The antibody-related dimeric molecular complexes of the invention have superior pharmacokinetic and biodistribution profiles when compared to those of monomeric single chain antibodies, diabodies, or full-sized dimeric IgGs. When compared to a whole IgG antibody, the molecular complexes of the invention provide a higher tumor to blood concentration ratio at an earlier time point after in vivo administration and show better penetration into a tumor. Such complexes also show a higher accumulation in the tumor with less accumulation in the kidney compared with both monomeric single chain antibodies or diabodies (See FIG. 9).

The antibody-related dimeric molecular complexes of the invention can be used diagnostically and therapeutically. For example, a dimeric molecular complex can be used for in vivo imaging, such as PET imaging, or for in vitro diagnostics. When conjugated to a therapeutic molecule, a dimeric molecular complex can be used to target the therapeutic molecule to a particular target.

In a preferred embodiment, the two fusion proteins within the dimeric complex each comprise single chain antibodies linked to the IgE CH4 domain via the hinge region and N-terminal amino acids including a portion of the first β sheet of the $CH_2$ domain of human $IgG_1$. The benefit of this attachment is that the disulfide bonds between the two fusion proteins will be located in the middle of the dimeric molecular complex, thus stabilizing the complex. Such dimeric molecular complexes typically have a molecular weight between 50 kD and 150 kD.

One example of an scFv-containing fusion protein used in a dimeric complex of the invention is SEQ ID NO:1 (FIG. 5B), which contains the single chain antibody 19G9scFv.

The hinge region in this fusion protein, THTCPPCPAPELLGGPSDSEY(SEQ ID NO:5; amino acid residues 260-280 of SEQ ID NO:1) contains the hydrophilic tetrapeptide 'DSEY' at amino acid residues 277-280, in place of the "wild-type" tetrapeptide 'VFLF' (amino acids residues 277-280 of SEQ ID NO:3).

This fusion protein is soluble and binds to antigen with an affinity similar to that of the parent immunoglobulin.

The linker between the VH and VL domains in the 19G9scFv fusion protein molecule consists of amino acid residues 125-144 of SEQ ID NO:1: GGGGSGGGGSGGGGSGGGGS (SEQ ID NO:8).

This particular fusion protein also comprises a C-terminal epitope-tag (GAPVPYPDPLEPRAA (SEQ ID NO:23)) at amino acid residues 391-405 of SEQ ID NO:1. Such epitope tags are often used to aid in purification of expressed molecules. In other embodiments of the invention, the dimeric molecular complexes of the invention are produced using fusion proteins which do not contain an epitope tag or with different epitope tags (e.g. ESSEEGGC (SEQ ID NO:24)).

The dimeric molecular complexes of the invention can also be made using Fab heavy chain fragments instead of single chain antibodies as the biological effector molecules in the fusion proteins which make up the dimeric complex (See Examples 5-8). When forming a dimeric molecular complex comprising Fab fragments, the CH1 domain of the heavy chain can be directly linked to the hinge region as in a normal immunoglobulin molecule, further reducing the amount of non-native, immunogenic sequences in the molecule. When Fab light chains are combined with the dimeric molecular complex of Fab heavy chains, an Fab dimeric molecular complex is formed.

Figure 8:
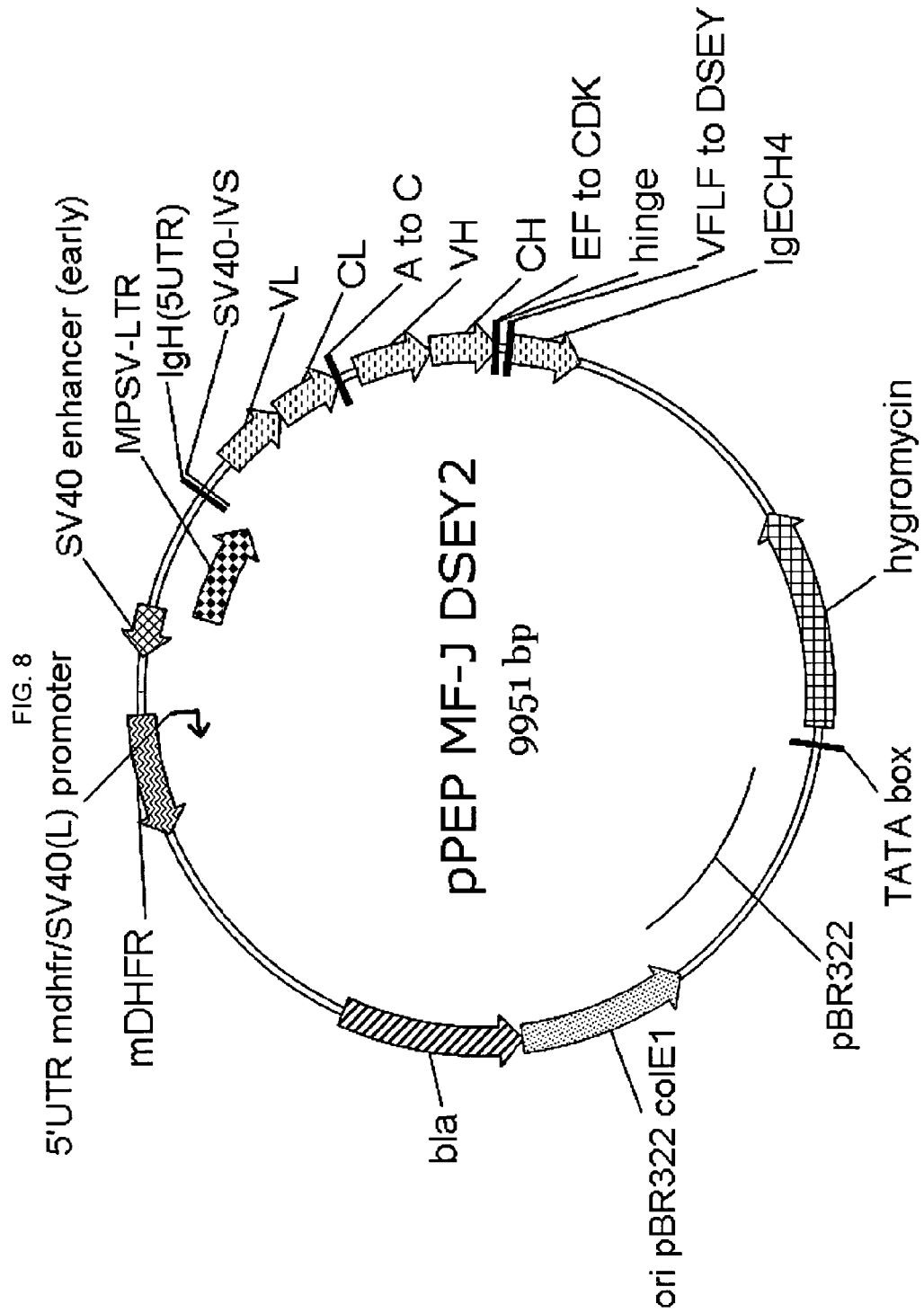
FIG. 8. Diagram of vector pPEP MF-J DSEY2 used to express the Fab dimer complex, as shown schematically in FIG. 1B.

A Fab dimer which has the same affinity as an IgG but a lower molecular weight can be constructed by eliminating the Fc region. The lower molecular weight of such a dimer can result in increased tumor penetration. Moreover, such Fab dimers will not bind to cellular Fc receptors (FcR), thus reducing unwanted FcR-related interactions. For example, a dimeric molecular complex using such Fab dimers can be used to make toxin conjugates which will not bind cells with FcγR or the neonatal Fc receptor (FcRn). FIG. 8 shows a vector used to generate such an Fab containing dimeric molecular complex, comprising a light chain (SEQ ID NOS: 19 and 21, amino acid and nucleic acid sequences respectively) and a heavy chain and IgE domain (SEQ ID NOS:20 and 22, amino acid and nucleic acid sequences, respectively). Such a complex has an internal disulfide bond between the light and heavy chains of the Fab, as well as disulfide bonds between the hinge regions of the two fusion proteins. This molecule will not elicit any Fc receptor or C1q mediated activities in vivo.

When the Fc binding domain is included in an Fc fusion protein, the dimeric molecular complex generated can bind not only to the Fc receptor but also to other proteins (e.g., FcγIIIa, FcγIIb, C1q, etc.) and can trigger the effector functions of these molecules. Binding to Fc receptors permits an antibody toxin conjugate to be directed to cells which express the Fc receptor. In vivo properties of an antibody that may be mediated by Fc receptor interaction include antigen dependent cellular cytotoxicity (ADCC), phagocytosis, complement dependent cytotoxicity, increased serum half-life, and decreased clearance, etc. The terms 'Fc fusion protein' or 'Fc fusion' are widely used to refer to the practice of dimerizing proteins using the IgG hinge and the CH2 and CH3 domains. Such 'Fc fusions' retain the ability to bind Fc receptors.

Preferred embodiments of Fab containing dimeric molecular complexes comprise hinge regions wherein the "wild-type" tetrapeptide 'VFLF' (SEQ ID NO:46) within the hinge region is replaced by the more hydrophilic "mutant" tetrapeptide DSEY (SEQ ID NO:47) or with the tetrapeptide 'KSKY' (SEQ ID NO:48), which provides extra lysines for conjugation (See SEQ ID NOS:5 and 7, respectively).

In other embodiments of either scFv or Fab containing dimeric molecular complexes, tetrapeptide sequences other than the two described above can be used to replace the hydrophobic tetrapeptide VFLF, which is present in the "wild-type" dimerization domain (amino acid residues 277-280 in SEQ ID NO:3) of the fusion protein. Replacement of this tetrapeptide with different tetrapeptides in the first and second fusion proteins which make up the dimeric construct is of particular utility in helping to promote heterodimer formation. In preferred embodiments, replacements include: SESE (SEQ ID NO:51) or SDSD (SEQ ID NO:52) on one fusion protein with SKSK (SEQ ID NO:53) or SRSR (SEQ ID NO:54) on the second fusion protein. Additional sequence substitutions for the hydrophobic tetrapeptide that can be used to promote heterodimer formation in this manner include: SESY (SEQ ID NO:55) or SDSY (SEQ ID NO:56) with SKSY (SEQ ID NO:57) or SRSY (SEQ ID NO:58); or DEEY (SEQ ID NO:49), DDDY (SEQ ID NO:59), DDEY (SEQ ID NO:60), DEDY (SEQ ID NO:61), EEEY (SEQ ID NO:62), EDDY (SEQ ID NO:63), EDEY (SEQ ID NO:64), or EEDY (SEQ ID NO:65) with RRRY (SEQ ID NO:66), RKRY (SEQ ID NO:67), RRKY (SEQ ID NO:68), RKKY (SEQ ID NO:69), KKKY (SEQ ID NO:70), KRRY (SEQ ID NO:71), KRKY (SEQ ID NO:50), or KKRY (SEQ ID NO:72). In the human $IgG_1$ structure, the two Phe residues in the hydrophobic tetrapeptide starting at $Val_{240}$ ($V_{240}FLF$) point inward, toward the corresponding Phe residues of the other heavy chain in the $IgG_1$ dimer. These Phe residues extend toward carbohydrate structures attached to CH2 and located between the two CH2 domains (Saphire (2002) *J Mol Biol* 319, pp. 9-18). The Val and Leu residues in the VFLF tetrapeptide point outward, away from the carbohydrates and toward amino acid residues in CH2. Replacement of residues within the VFLF tetrapeptide with less hydrophobic residues (Ser, Thr, Asp, Glu, Asn, Gin, Gly, His, Lys, Arg, Cys or Ala) decreases the number of exposed hydrophobic side chains, thus improving the solubility of the dimeric molecular complex. Substitution with Lys or Cys also provides sites for chemical modifications. To promote heterodimer formation, one or both Phe residues within one fusion protein of the dimeric molecular complex are replaced by residues possessing a charge opposite that present in the second fusion protein in the dimeric molecular complex. Placement of oppositely charged residues pointing toward each other from each fusion protein comprising the heterodimer allows the charge interaction to promote heterodimer formation. In general, if X is any amino acid that is not hydrophobic, then the following combinations of sequences could be used to make heterodimers by substitution for the VFLF tetrapeptide in the two molecules of the heterodimer: 1) XEXY or XDXY with XKXY or XRXY; 2) XEXE, XEXD, XDXE or XDXD with XRXR, XRXK, XKXR or XKXK; or 3) XRXE, XRXD, XKXE or XKXD with XEXR, XEXK, XDXK or XDXR.

In other embodiments, the wild-type hydrophobic tetrapeptide sequence 'VFLF' and the adjacent proline residue (amino acid residues 277-281 of SEQ ID NO:3) can be replaced with amino acid sequences from the loop connecting CH3 and CH4 in the human IgE sequence (SEQ ID NO:45). This stretch of five amino acids (VFLFP) can be replaced with either LysThrSerGly (amino acid residues 315 to 318 of SEQ ID NO:45) or ThrLysThrSerGly (amino acid residues 314 to 318 of SEQ ID NO:45). Similarly, residues 277 to 281 in SEQ ID NO:1 (DSEYP) or amino acid residues 263 to 267 in SEQ ID NO:20 (DSEYP) can also be replaced by these IgE-derived sequences in order to create dimeric molecular complexes composed entirely of native sequence from either human IgG or IgE.

Figure 1C:
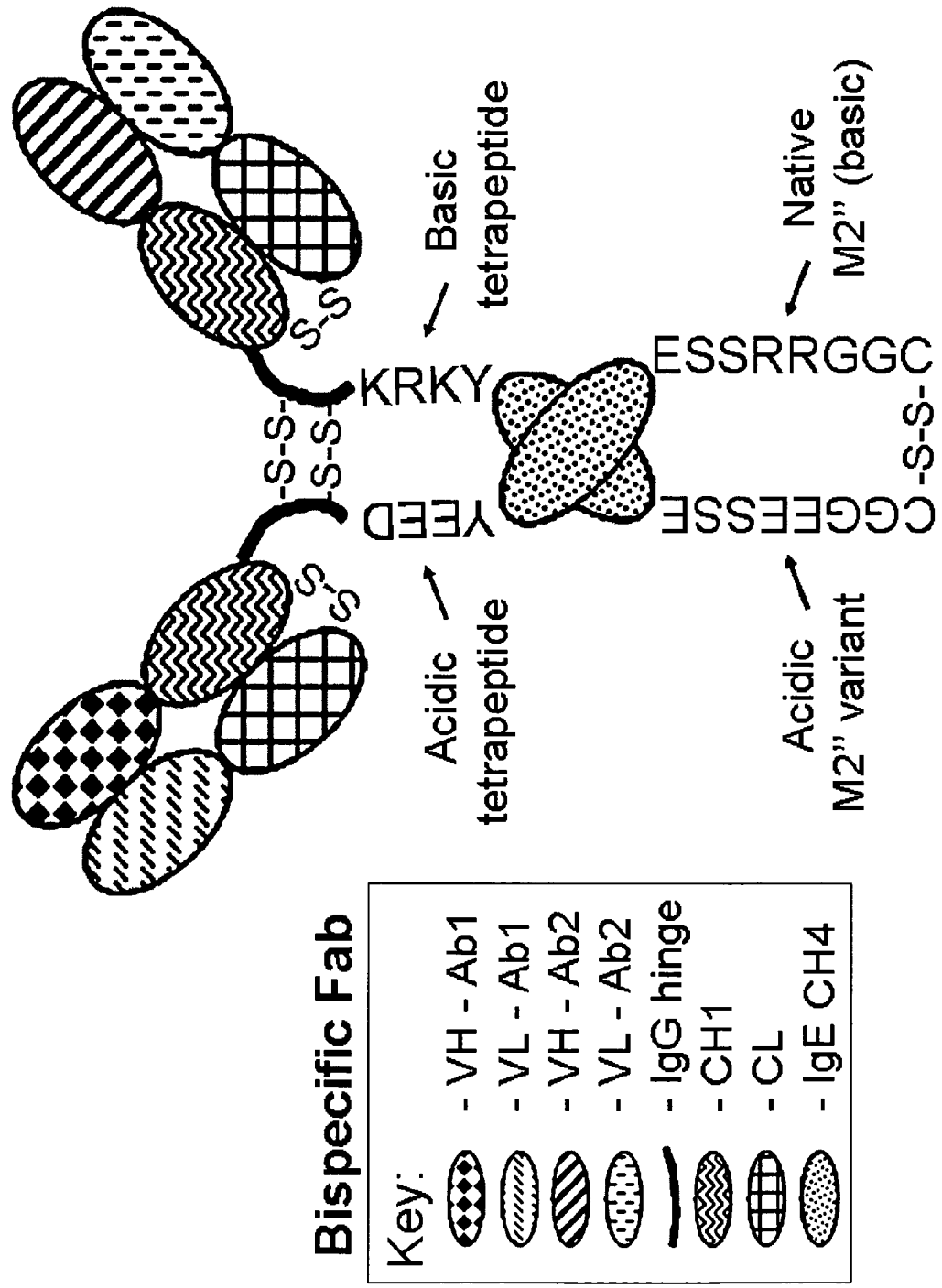

Typically, an IgE CH4 domain is used to dimerize fusion proteins of the invention. However, in order to further stabilize heterodimers, M2" IgE CH4 splice variants can be added at the C-termini of the fusion proteins comprising the dimeric molecular complex. In one fusion protein, an acidic form of the M2" IgE CH4 splice variant (ESSEEGGC (SEQ ID NO:26)) is added to the C terminus, while on the second fusion protein an M2" IgE CH4 splice variant containing basic amino acids (ESSRRGGC (SEQ ID NO:27) is added. See FIG. 1C.

Dimeric Molecular Complexes Using Other Biological Effector Moieties

A variety of biological effector moieties other than antibody-related molecules can be used in the fusion proteins which comprise the dimeric molecular complexes of the invention. In such proteins, an amino acid linker between the biological effector moiety and the hinge region may or may not be used. If included, the amino acid linker is preferably a poly Gly linker from 1 to 10 or more amino acids and may include other amino acids, including Ala, Ser, Thr and Asp.

Depending on the intended use, dimeric molecular complexes may be comprised of fusion proteins where the two biological effector moieties are the same or different (i.e. homodimers or heterodimers, respectively). Heterodimers are stabilized in a manner similar to that described above.

A. Extracellular Domains of Type I Membrane Receptors

Figure 1D:
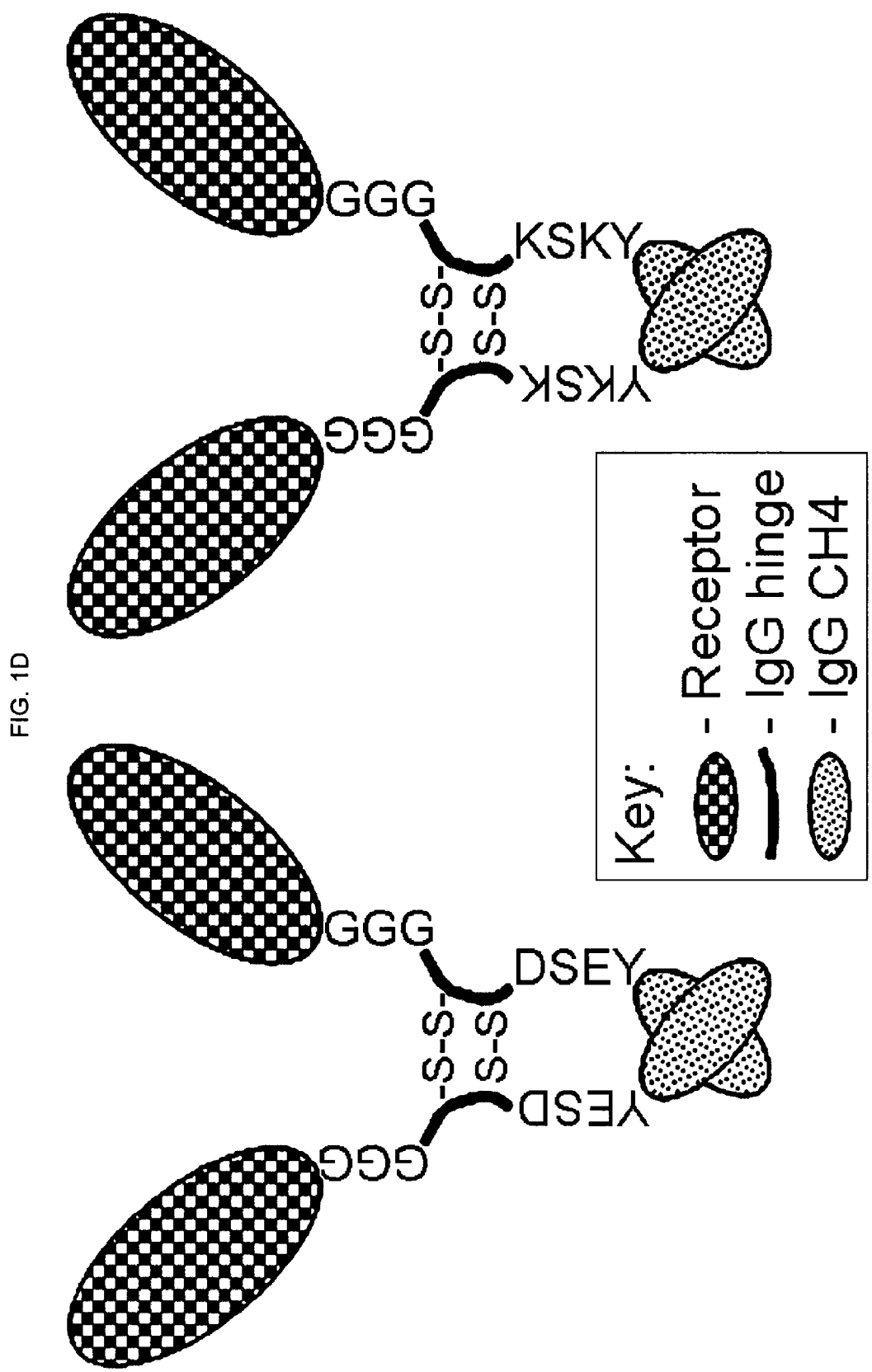

A dimeric molecular complex comprised of fusion proteins in which the biological effector moiety is an extracellular domain of a type I membrane receptor is shown schematically in FIG. 1D and such complexes are useful as biological effectors or to bind ligands. Type I membrane receptors useful in the invention include TNF receptors, ephrins, Ephs, VEGF receptors, IGF receptors, thrombospondin, thrombomodulin, PDGF receptors, IL-2R, TCR complex components, EGF receptors, TGF receptors, tissue factor, growth factor receptors, HGH receptor, IFN receptors, HER2, insulin receptor, etc.

B. Cytokines

In some embodiments, the biological effector moiety is a cytokine useful for modulating biological responses of cells. Cytokines useful in the invention include lymphokines such as macrophage activating factor (MAF), macrophage migration inhibition factor (MMIF), leukocyte migration inhibition factor (MCF), leukocyte migration inhibition factor (LMIF), a histamine releasing factor (HRF), or transfer factor (TF). Tumor necrosis factors, such as TNF-α (cachectin) and TNF-β (lymphotoxin) can be biological effector moieties. Interleukins, such as IL-1, IL-2, IL-3, IL-4, IL-5, IL-6, IL-7, IL-8, IL-9, IL-10, IL-11, IL-12, IL-13, IL-14, and IL-15, IL-17, can be biological effector moieties. Interferons, such as IFN-α, IFN-β, IFN-γ, IFN-ω, and IF-τ, can be biological effector moieties.

Other useful cytokines include colony stimulating factors, chemokines, and stress proteins. Examples of colony stimulating factors include granulocyte colony stimulating factor (G-CSF), granulocyte macrophage colony stimulating factor (GM-CSF), macrophage colony stimulating factor (M-CSF), and multi-CSF (IL-3).

Examples of α-chemokines include IL-8, NAP-2 (neutrophil activating protein 2), PF-4 (platelet factor 4), and βTG (β-thromboglobulin). β-Chemokines include MCP-1 (monocytes chemoattractant protein 1), MCP-3, MIP-1α (macrophage inflammatory protein 1α), MIP-1β, and RANTES ("Regulated upon Activation Normal T Expressed and presumably Secreted chemokine"). Other useful chemokines include, e.g., CCL chemokines; CXC (SCYB) chemokines or CX3C chemokines; XC chemokines; and CC chemokines, such as CCL2, CCL7, CCL11, CCL8, CCL13, CCL1, CCL5, CCL16, CCL14, CCL15, CCL23, CCL18, CCL3 and CCL4.

Stress proteins include heat shock proteins (HSPs), glucose-regulated proteins (GRPs), ubiquitin, and superoxide dismutase.

C. Enzymes

In other embodiments, a biological effector moiety is an enzyme, e.g., a proteolytic enzyme (an amino peptidase, an aspartyl protease, a serine protease, a metallo protease, a cysteinyl protease, pepsin, trypsin, thrombin, lysozyme, Factor VII, Factor X, Factor IX). Other enzymes, such as glycosidases, esterases, hydrolases, nucleases, syntheases, isomerases, polymerases, kinases, phosphatases, reductases, including oxido-reductases, transferases, ligases, restriction enzymes, amidases, ATPases, carbohydrases, lipases, cellulases, dehydrogenases, and oxidases also can be used.

D. Toxins

Therapeutically useful toxins can also be used as biological effector moieties in the fusion proteins comprising the dimeric molecular complexes of the invention. There are numerous examples of such toxins, well known to those skilled in the art, such as the bacterial toxins *Pseudomonas* exotoxin A and diphtheria toxin, and the plant toxins ricin, abrin, modeccin, saporin, and gelonin.

E. Extracellular Domains of Type II Membrane Receptors

Figure 2:
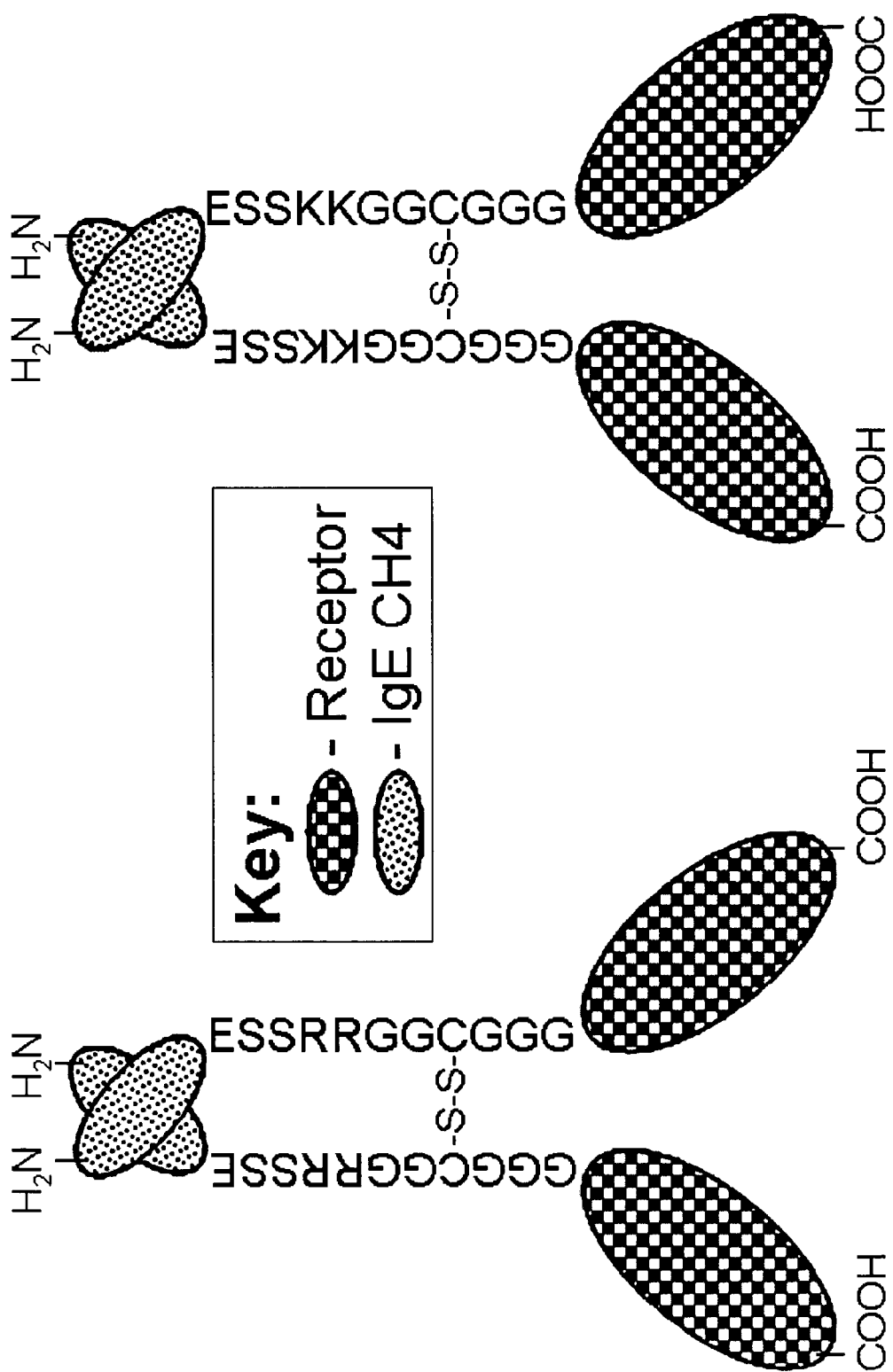
FIG. 2. Schematic of a dimeric molecular complex in which the biological effector moiety is an extracellular domain of a type II membrane receptor.

A dimeric molecular complex also can be constructed wherein the biological effector moiety is an extracellular domain of a type II membrane receptor. In this case, however, each of the two fusion proteins comprises, from N to C terminus, (a) a CH4 dimerization domain with a C terminal extension comprised of an M2" IgE CH4 splice variant (ESSRGGC (SEQ ID NO:27)), (b) an amino acid linker (preferably 3-10 residues in length) which is covalently bound to the CH4 dimerization domain and (c) an extracellular domain of the type II membrane receptor. See FIG. 2. In some embodiments, the sequence of the M2" IgE splice variant can be modified to provide additional sites for chemical modification (e.g. ESSKKGGC (SEQ ID NO:28), ESSCRGGC (SEQ ID NO:29) or ESSRCGGC (SEQ ID NO:30)).

Type II membrane receptors comprise only ~5% of transmembrane proteins, but include members with important biological effector functions such as hepsin protease, ectodysplasin, collagenous membrane proteins, macrophage scavenger receptors, MARCO protein, TNF ligand-like proteins, asialoglycoprotein receptors, lymphocyte IgE receptor, Kupffer cell receptor, NKG2, NKR-P1, Ly-49, CD69, CD72, LyB-2, collectins, CLEC5A, etc.

Production of Dimeric Molecular Complexes

Fusion proteins for dimeric molecular complexes of the invention can be produced recombinantly or synthetically, or using a combination of the two approaches. For recombinant production, the invention provides nucleic acid molecules which encode fusion proteins of the invention (see below).

It is possible to produce a fusion protein of the invention using chemical methods to synthesize the amino acid sequence of the fusion protein. Methods include direct peptide synthesis using solid-phase techniques (Merrifield, *J. Am. Chem. Soc.* 85, 2149-2154, 1963; Roberge et al., *Science* 269, 202-204, 1995). Protein synthesis can be performed using manual techniques or by automation. Automated synthesis can be achieved, for example, using Applied Biosystems 431A Peptide Synthesizer (Perkin Elmer). Optionally, fragments of a fusion protein can be separately synthesized and combined using chemical methods to produce a full-length fusion protein. See WO 01/98340.

Nucleic Acid Molecules

Nucleic acid molecules of the invention can comprise any nucleotide sequence which encodes the desired fusion protein. Nucleic acid molecules of the invention include single- and double-stranded DNA (including cDNA) and mRNA. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Methods which are well known to those skilled in the art can be used to construct nucleic acid molecules of the invention. These methods include in vitro recombinant DNA techniques and synthetic techniques. Such techniques are described, for example, in Sambrook et al. (1989) and in Ausubel et al. CURRENT PROTOCOLS IN MOLECULAR BIOLOGY, John Wiley & Sons, New York, N.Y., 1989.

In some embodiments, the nucleic acid molecules are expression constructs which contain the necessary elements for the transcription and translation of an inserted coding sequence encoding a fusion protein. Fab dimer expression constructs can include a coding sequence for the light chain with a C-terminal cysteine. An expression construct can be present in a vector suitable for introducing fusion proteins of the invention into a cell.

Fusion proteins of the invention can be recombinantly expressed in a variety of host cells. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems, particularly mammalian systems, including human systems. See WO 01/98340, which is incorporated herein by reference in its entirety. The choice of vector components and appropriate host cells is well within the capabilities of those skilled in the art.

In some embodiments of this invention, both fusion proteins of a dimeric molecular complex are expressed in the same cell, preferably from the same plasmid, e.g., as a dicistronic operon (Skerra et al., Protein Eng. 4, 971, 1991). A signal sequence can be included to direct the fusion proteins to the desired cellular location. Expression of the two fusion proteins of a dimeric molecular complex from the same plasmid leads to an increased amount of the bispecific dimer being formed, as equivalent amounts of each component are being produced within the cell.

Optionally, a fusion protein can comprise a moiety which can be used as a detection or purification tag, such as peptides comprising at least five histidine residues, or the commonly used c-myc and FLAG tags.

Diagnostic Methods

The dimeric molecular complexes of the invention can also be useful for diagnostic purposes. For example, the complex can comprise two fusion proteins, one protein comprising a biological effector moiety designed to bind to an analyte of interest and the other protein comprising a biological effector molecule that is, or is bound to, a detectable label which can easily be quantified, e.g. an enzyme, a fluorescent protein, a radionuclide, etc.

Therapeutic Methods

Dimeric molecular complexes of the invention can be provided in a pharmaceutical composition for administration to a mammal, preferably a human. Complexes composed of antibody fragments (either mono- or bi-specific) are particularly useful in tumor therapy. For example, one fusion protein of the complex can comprise a molecule which binds to a tumor marker and the other fusion protein can comprise a molecule which binds to a T-cell epitope, a toxin, or a radionuclide binding peptide or protein to bring a killing function close to the tumor cell.

For preparing suitable pharmaceutical compositions comprising dimeric molecular complexes of the invention, one skilled in the art can use known injectable, physiologically acceptable sterile solutions. For preparing a ready-to-use solution for parenteral injection or infusion, aqueous isotonic solutions, such as, e.g., saline or corresponding plasma protein solutions are readily available. The pharmaceutical compositions may be present as lyophylisates or dry preparations, which can be reconstituted with a known injectable solution directly before use under sterile conditions. A pharmaceutical composition can be supplemented with known carrier substances or/and additives (e.g., serum albumin, dextrose, sodium bisulfite, EDTA, etc.).

Pharmaceutical compositions of the invention can be administered by different routes of application known to one skilled in the art, particularly by intravenous injection or direct injection into target tissues. For systemic application, intravenous, intravascular, intramuscular, intraarterial, intraperitoneal, oral, or intrathecal routes can be used. More local administration can be effected subcutaneously, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, compositions may be administered once or several times, also intermittently, for instance on a daily basis for several days, weeks or months and in different dosages.

The dosage will depend on age, condition, sex and extent of the disease in the patient and can vary from 0.1 mg/kg to 200 mg/kg, preferably from 0.1 mg/kg or 100 mg/kg/dose, in one or more dose administrations daily, for one to several days.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Production of scFv Dimeric Molecular Complexes

This example demonstrates the production of two dimeric molecular complexes with the structure shown in FIG. 1A. Two constructs were prepared. In both constructs, a poly-Gly linker was added to the N-terminus of the wild-type $IgG_1$ hinge region. In a "wild-type" construct, this was followed by the native sequence of some of the first beta strand of CH2 of human IgG1. In the "mutant" construct, mutations were introduced to eliminate hydrophobic residues present in the "wild-type" beta strand which would otherwise be exposed to solvent and could potentially hinder solubility. Two hydrophobic residues, $Val240$ and $Leu_{242}$ within the heavy constant region of $IgG_1$ (SEQ 10 NO:25), have hydrophobic interactions with the IgG CH2 domain, and two phenylalanines, $Phe_{241}$ and $Phe_{243}$, interact with the carbohydrate groups. These hydrophobic amino acids Val, Phe, Leu, and Phe at positions 240-243 of SEQ ID NO:25 were replaced by the hydrophilic residues Asp, Ser, Glu, and Tyr, respectively. Two cysteine groups in the hinge region result in covalent links between each fusion protein upon dimerization of the CH4 regions.

Generation of the Single Chain Antibody

A single chain antibody termed 19G9scFv was generated from VH and VL chains which were amplified by PCR using primers which introduced restriction sites and sites for overlap extension of the 16-amino acid linker GGGGSGGGGSGGGGSGGGGS (SEQ ID NO:8). After 15 cycles of extension the scFv was amplified with the original forward and back primers and cloned by restriction digest inot the bacterial expression vector pz613. See FIG. 3.

VH forward primer:
                                              (SEQ ID NO: 15)
GCGGCCCAGCCGGCCATGGCCCAGGTTCAGCTGGTGCAGTC;

VH back primer:
                                              (SEQ ID NO: 16)
CCACCGGAGCCGCCGCCGCCAGAACCACCACCACCAGAACCACCACCAC
CTGAAGAGACGGTGACC;

-continued

VL forward primer:
(SEQ ID NO: 17)
GGCGGCGGCGGCTCCGGTGGTGGTGGATCCGAAATTGTGTTGACGCAGT
C;

VL back primer:
(SEQ ID NO: 18)
GCGGCCGCTTTGATCTCCACCTTGGTCC.

Generation of the CH4 Dimerization Domain

Figure 4A:
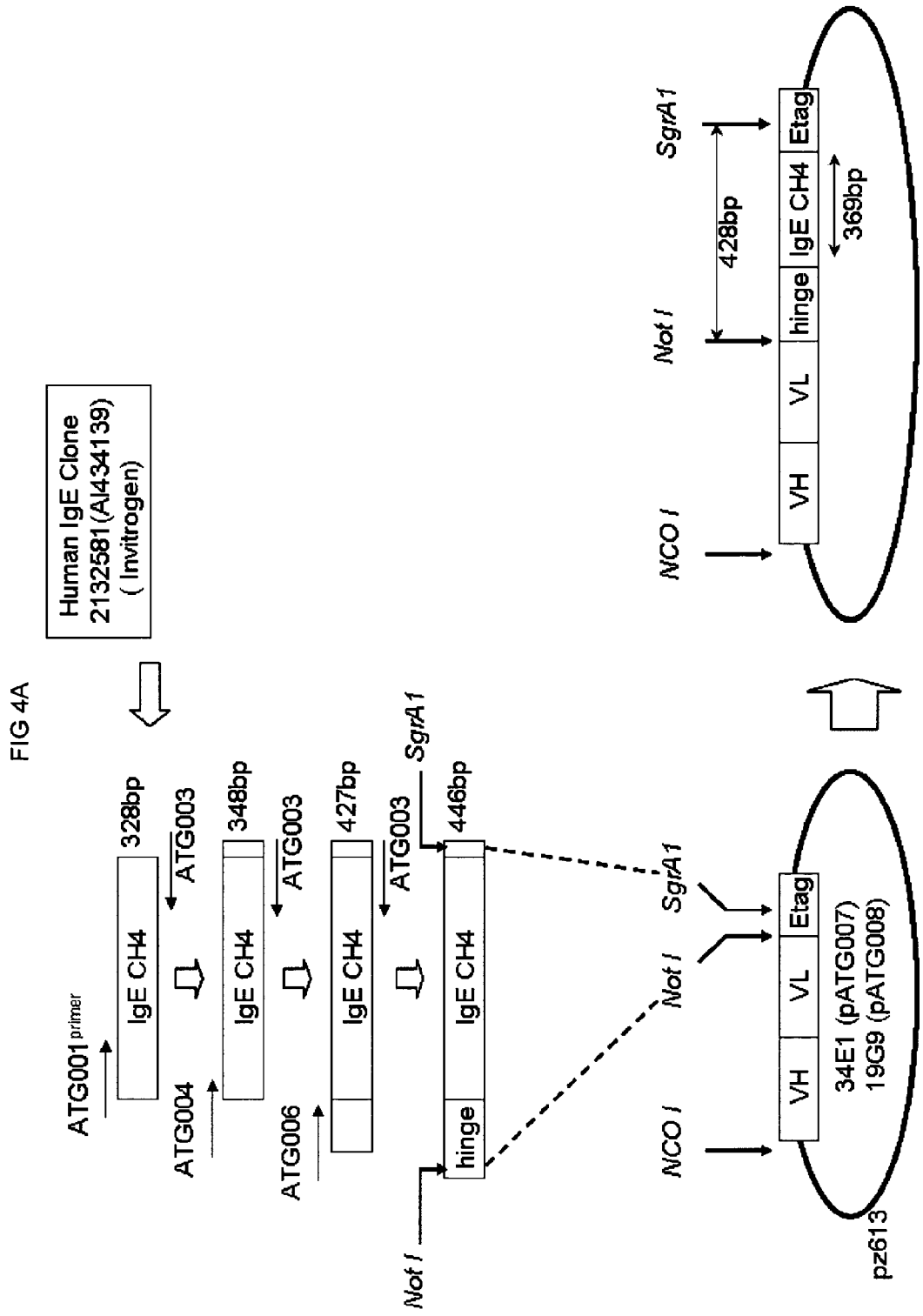
FIG. 4A-B. Schematics showing construction of IgE CH4 dimerization domain constructs used to make the dimeric molecular complex containing the 19G9scFv single chain antibody.
Figure 4B:
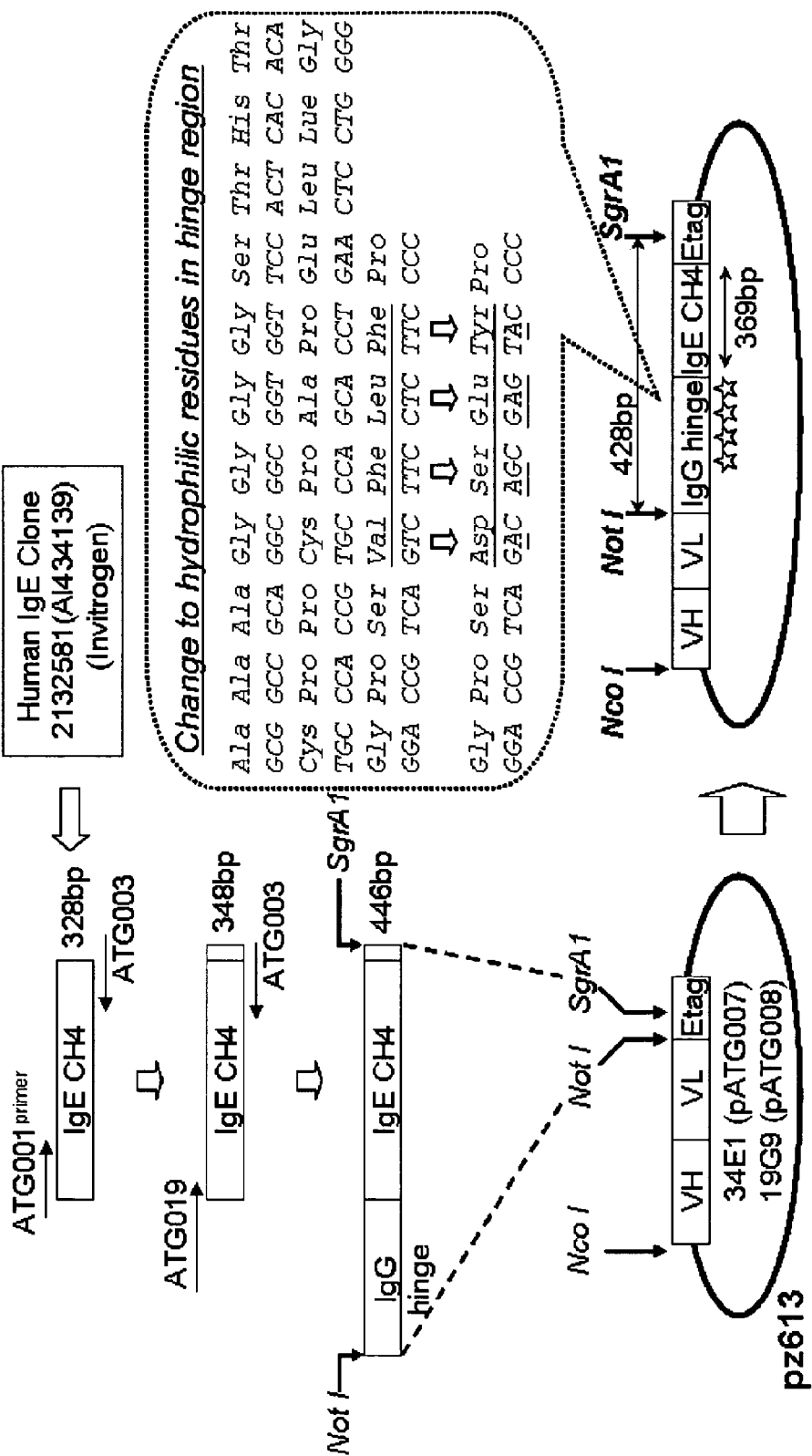

The CH4 domain of IgE was cloned from mRNA purchased from Invitrogen (clone 2132581) using PCR primers "ATG001" (IgECH4_bk_a): CCGTCAGTCT TCCTCT-TCCC CCCGCGTGCT GCCCCGGAAG (SEQ ID NO:9) and "ATG003" (IgECH4_for_a): CGGATACGGC ACCG-GCGCAC CTTTACCGGG ATTTACAGAC (SEQ ID NO:11). The IgG$_1$ hinge region and the first beta strand of IgG$_1$ CH2 was introduced by PCR using primer "ATG002": TTCCTCTTCC CCCCGCGTGC TGCCCCGGAA G (SEQ ID NO:10). Not1 and SgrA1 sites were introduced by primers ATG001 and ATG003, respectively. These sites permitted direct cloning by restriction digestion of the IgG$_1$ hinge-IgE CH4 region fusion into the single chain vector ("19G9"). See FIG. 4.

The amino acid sequence of the "wild-type" 19G9scFv fusion protein, sometimes referred to as 19G9M1 (SEQ ID NO:3) is shown in FIG. 5A. The amino acid sequence of the "mutated" fusion protein, referred to as 19G9M2 (SEQ ID NO:1), which contains the sequence DSEY at amino acid residues 277-280 in the dimerization domain, is shown in FIG. 5B.

EXAMPLE 2

Expression, Purification, and Function of scFv Dimeric Molecular Complexes

Figure 6A:
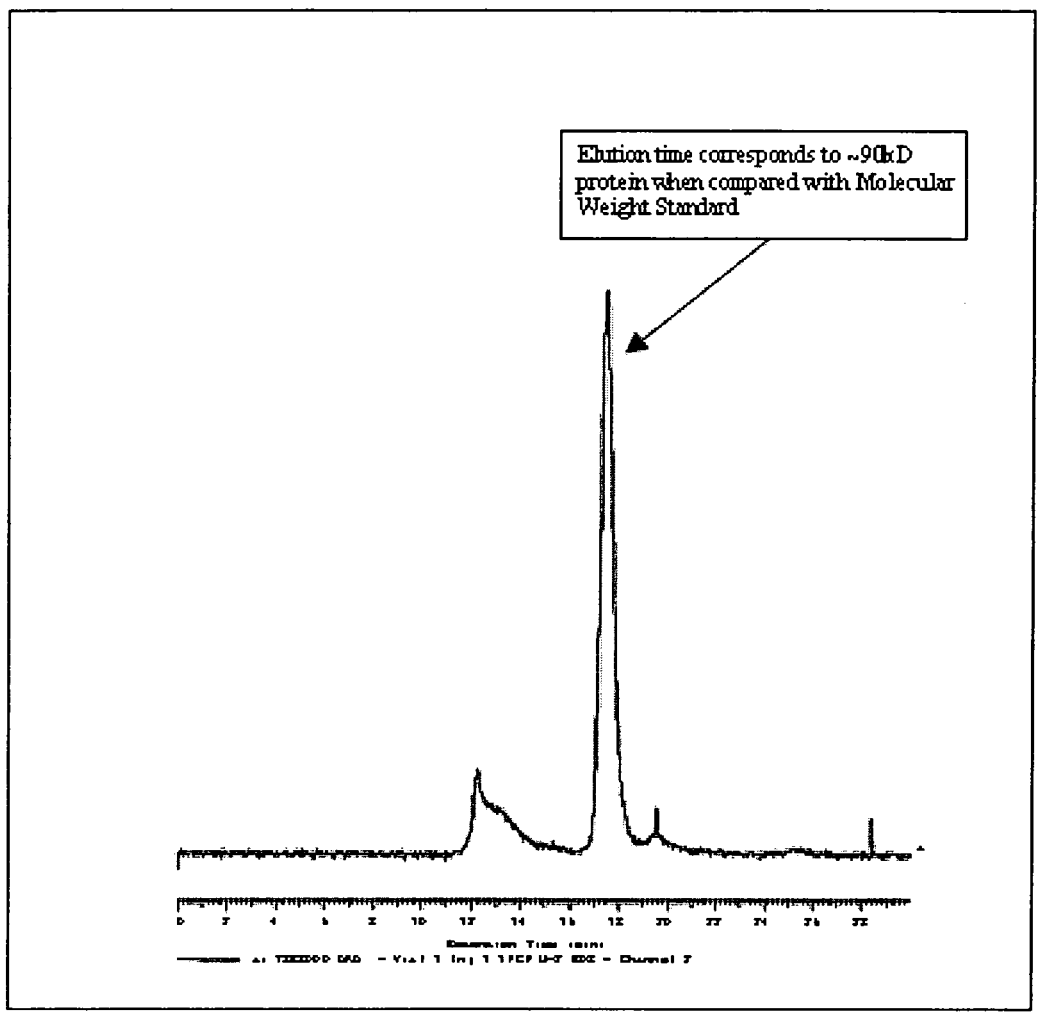

The "mutant" 19G9scFv dimeric molecular complex construct (19G9M2; SEQ ID NO:1) described in Example 1 was cloned into the mammalian expression vector pPEP1poly and expressed in CHO cells. Purification was carried out using epitope-tag affinity chromatography, and the purified complex was tested for binding, antigen specificity, and affinity using an ELISA. See FIG. 6A. The molecular weight of the purified complex (reduced and non-reduced) was analyzed in an SDS-PAGE system. 4%-12% SOS-PAGE was used, with a running buffer of MES SDS at 40 minutes at 120 mA, 200V. See FIG. 6B.

Figure 7:
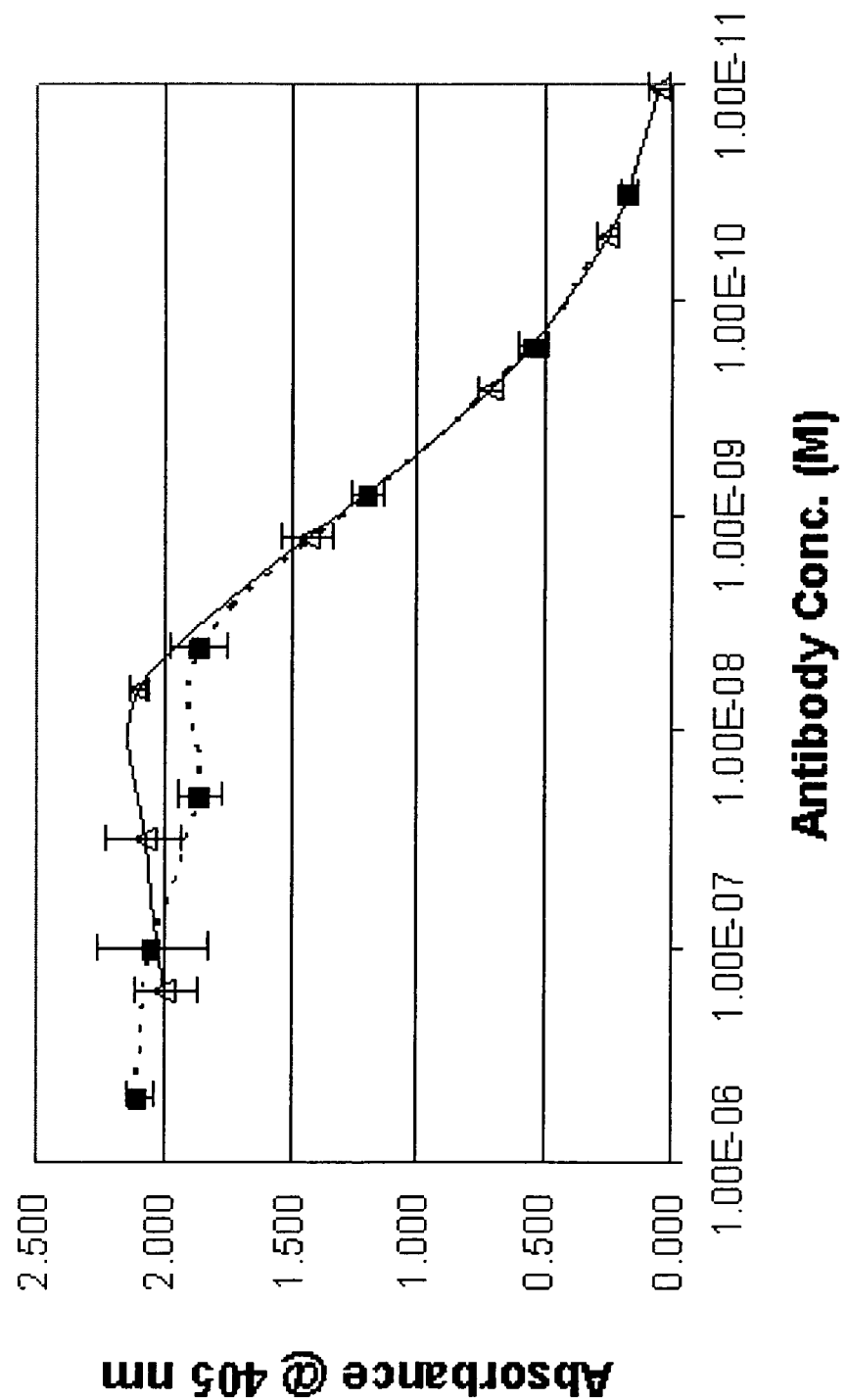
FIG. 7. Graph showing ELISA data of purified 19G9 scFv dimeric molecular complex (open triangles) binding to BHK-RG-1 protein compared with binding of the corresponding 19G9 diabody (closed squares). Much of the 19G9 diabody sequence is similar to the 19G9 scFv sequence (amino acids 1-251 in SEQ ID NO:1). The linker between the VH and VL domains in the diabody, however, is only 5 amino acids in length (GGGGS, SEQ ID NO:73).

FIG. 7 shows the results of binding of the 19G9M2 dimeric molecular complex to BHK-RG-1 protein compared with the binding of the corresponding diabody (the dimeric single chain antibody made from the 19G9 VH and VL linked by a shortened five amino acid linker). The diabody and the IgG of 19G9 have equivalent activity. The EC$_{50}$ is roughly nanomolar. The antibody concentration was calculated based upon molecular weights of 80 kD for the dimeric molecular complex and 50 kD for the diabody. The secondary antibody used in the assay was HRP-anti-E tag antibody.

EXAMPLE 3

Demonstration of Disulfide Bond Formation in the Hinge Region

FIG. 6B is a Coomassie blue-stained SDS-polyacrylamide gel demonstrating that the dimeric molecular complex preparation described in Examples 1 and 2 comprises predominantly disulfide dimers (lanes 2 and 3) with only a small contamination by monomer. Upon reduction, all the disulfide dimers collapse to monomers (lanes 5 and 6). This result demonstrates that the hinge region from the IgG$_1$ functions properly and that disulfide bonds form in the hinge after the IgE CH4 domain dimerizes. Lanes, from left to right: 1, 10 µl marker; 2, 2 µl 19G9 M2; 3, 5 µl 19G9 M2; 4, blank; 5, 2 µl reduced 19G9 M2; 6, 5 µl reduced 19G9 M2; 7, 10 µl marker.

EXAMPLE 4

In Vivo Biodistribution of the 19G9 Dimeric Molecular Complex

Methods for radiolabeling and chelator attachment were adapted from Nikula et al. (1995), *Nucl. Med. Biol.*, 22, 387-390. Purified 19G9scFv dimeric molecular complex, 19G9 IgG, 19G9scFv and the 19G9 diabody were characterized by SEC and SDS-PAGE prior to use. Labeling was performed using $^{111}$In, in buffers and equipment which were rendered metal-free by repeated rinsing with 10 mM EDTA solution and Chelex-treatment prior to filtration. The chelator p-SCN-CHX-A"-DPTA was purchased from Macrocyclics Inc. The buffer used for conjugation contained 50 mM carbonate, 150 mM NaCl, pH 6.5. Radiolabeling was performed in a buffer containing 50 mM NaAc, 150 mM NaCl, pH 6.5.

Figure 9:
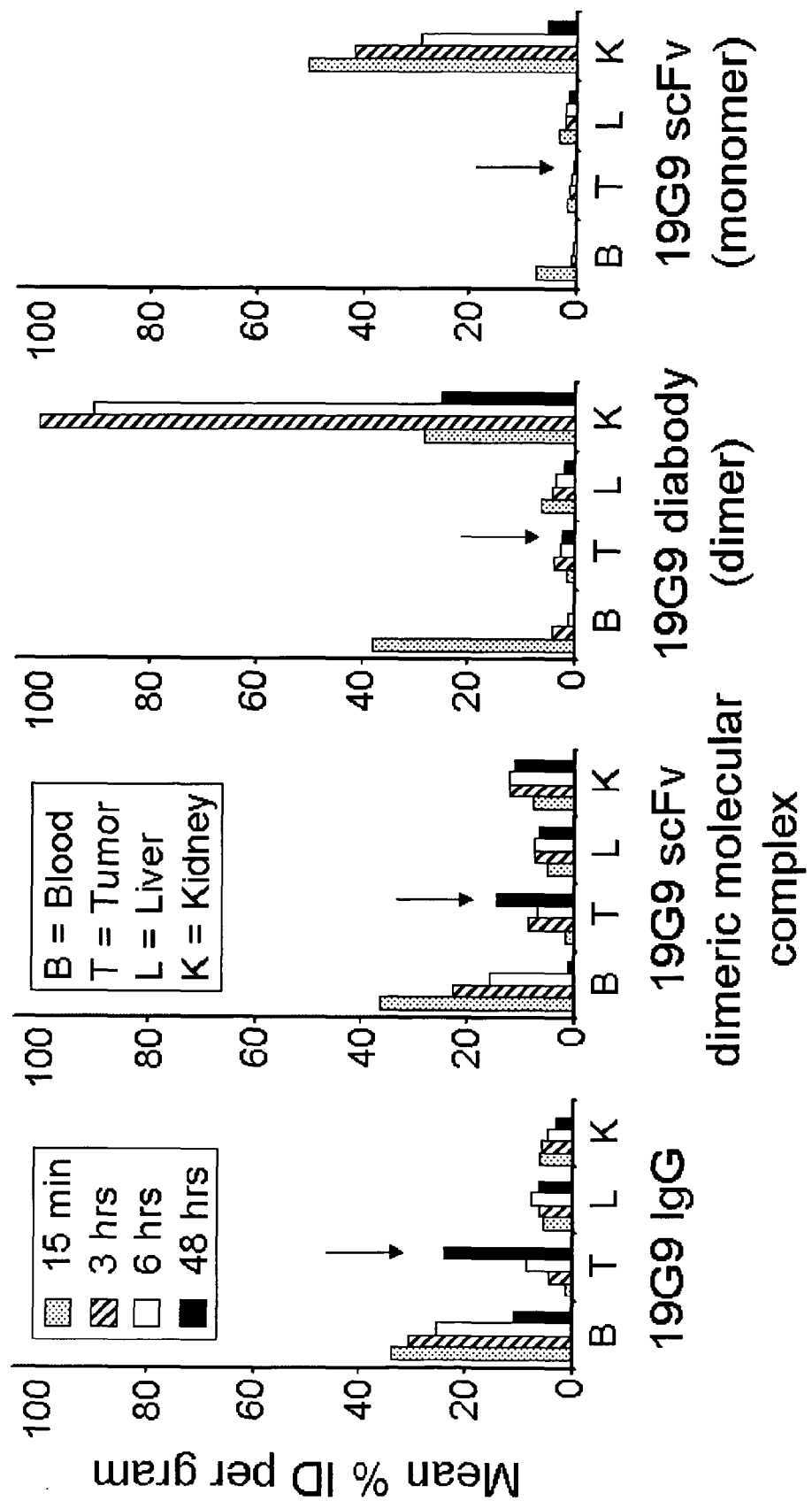
FIG. 9. In vivo bio-distribution of the 19G9scFv dimeric molecular complex as compared with other antibody formats (19G9 IgG, 19G9 monomeric scFv single chain antibody and 19G9 diabody). The Y-axis plots the average percent injected dose per gram (mean % ID per gram) for four tissues: blood (B), tumor (T), liver (L) and kidney (K). Values are shown for tissues harvested at 0.25, 3, 6 and 48 hrs following injection of 2 μCi of $^{111}$In-labeled antibody per animal. The % ID per gram for the 48 hr tumor sample is indicated with an arrow. While the tumor is well labeled by both the 19G9 scFv dimeric molecular complex and the 19G9 IgG, a high percentage of the 19G9 IgG is also retained in the blood at 48 hr, in contrast to the dimeric molecular complex. The scFv and diabody do not label the tumor well and also result in an accumulation of label in the kidneys.

$^{111}$In-radiolabeled antibody solutions (PBS) of the four antibody groups described above were injected into 8 LNCaP tumor bearing mice per group (2 µCi per animal). Two animals per group were weighed, sacrificed and tissues harvested at 15 min, 3 hr, 6 hr and 48 hr following injection of labeled antibody. The tumor, tissue or blood sample was weighed and the total radioactivity determined. The mCi per gram of sample was compared with the total mCi per animal weight to determine the percentage of the injected dose per gram tissue and the average calculated for each group and time point (mean % ID per gram). The results are shown in FIG. 9.

EXAMPLE 5

Production of Fab Fusion Proteins and Expression of Fab Dimeric Molecular Complexes This example demonstrates the production of Fab dimeric molecular complexes with the structure shown in FIG. 1B (i.e. a monospecific dimeric molecular complex in which the biological effector moiety is a Fab fragment). This construct does not have any linker sequence between the C-terminus of the CH1 domain of the Fab and the N-terminus of the IgG$_1$ hinge region and the sequence in this region is the same as in an IgG.

In the IgG$_1$ hinge region, four hydrophobic amino acids, Val, Phe, Leu and Phe, (amino acid residues 263-266 of SEQ ID NO:20) located at the C-terminus of the hinge region were replaced by the hydrophilic residues Asp, Ser, Glu, and Tyr respectively, to avoid potential difficulty in solubility. The two cysteine groups present in the hinge region result in covalent links between each fusion protein upon dimerization of the CH4 regions. Another cysteine is also located at the C-terminus of both CH1 and CL to allow these domains to be linked by a covalent disulfide bond.

(a) Insertion of IgG1 Hinge Region and IgE CH4 Domain into IgG1 Expression Vector DNA coding for the IgG1 hinge region and the IgE CH4 domain was amplified by PCR using primers which introduced PciI and FseI restriction sites, and this region was then cloned by restriction digestion into the cloning vector pCR2.1_TOPO. to produce pCR2.1_hinge_IgE CH4 to create the heavy chain of the Fab fusion protein of the J_DSEY dimeric molecular complex.

```
ATG47 forward primer:
                                      (SEQ ID NO: 31)
CTCACACATGTCCACCGTGCCCAGCACCTGAAC;

ATG46 reverse primer:
                                      (SEQ ID NO: 32)
TGTGGCCGGCCCTATTTACCGGGATTTACAGACACCGCT;
```

The VH and CH domains of a Fab antibody (ABJ), was amplified by PCR using primers which introduced a PciI restriction site, and cloned by restriction digestion (EcoRV and PciI) into pCR2.1_hinge_IgE CH4.

```
ATG51 forward primer:
                                      (SEQ ID NO: 33)
GTTGAAATTAAACGTACGGTGGCTGC;

ATG56 reverse primer:
                                      (SEQ ID NO: 34)
GACATGTGTGAGTTTTATCGCAGCTTTTCGGTTCCACTTTTTTATCC;
```

Figure 10:
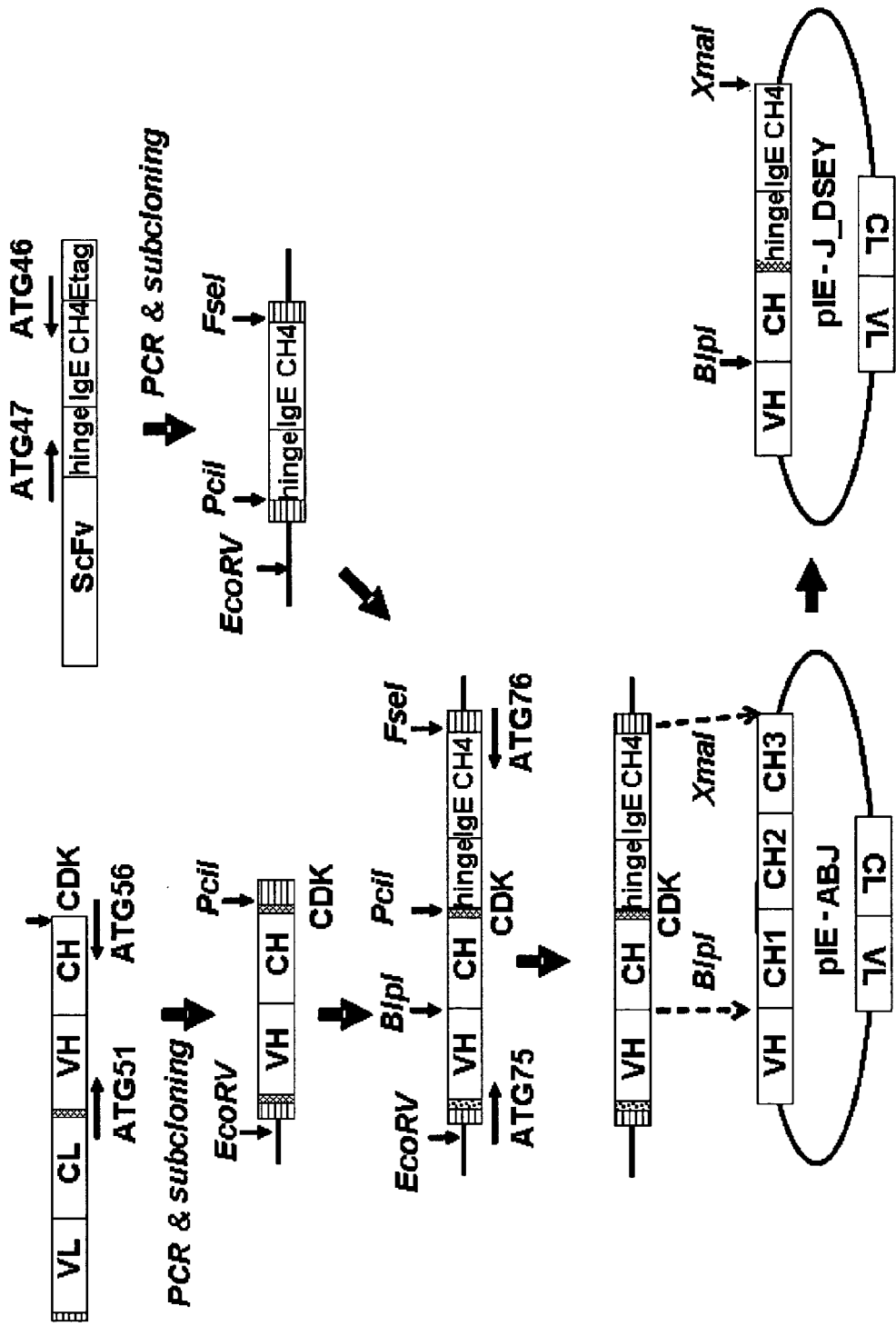
FIG. 10. Schematic showing generation of the pIE-J_DSEY plasmid used to express the J_DSEY fusion protein, as described in Example 5.
Figure 11:
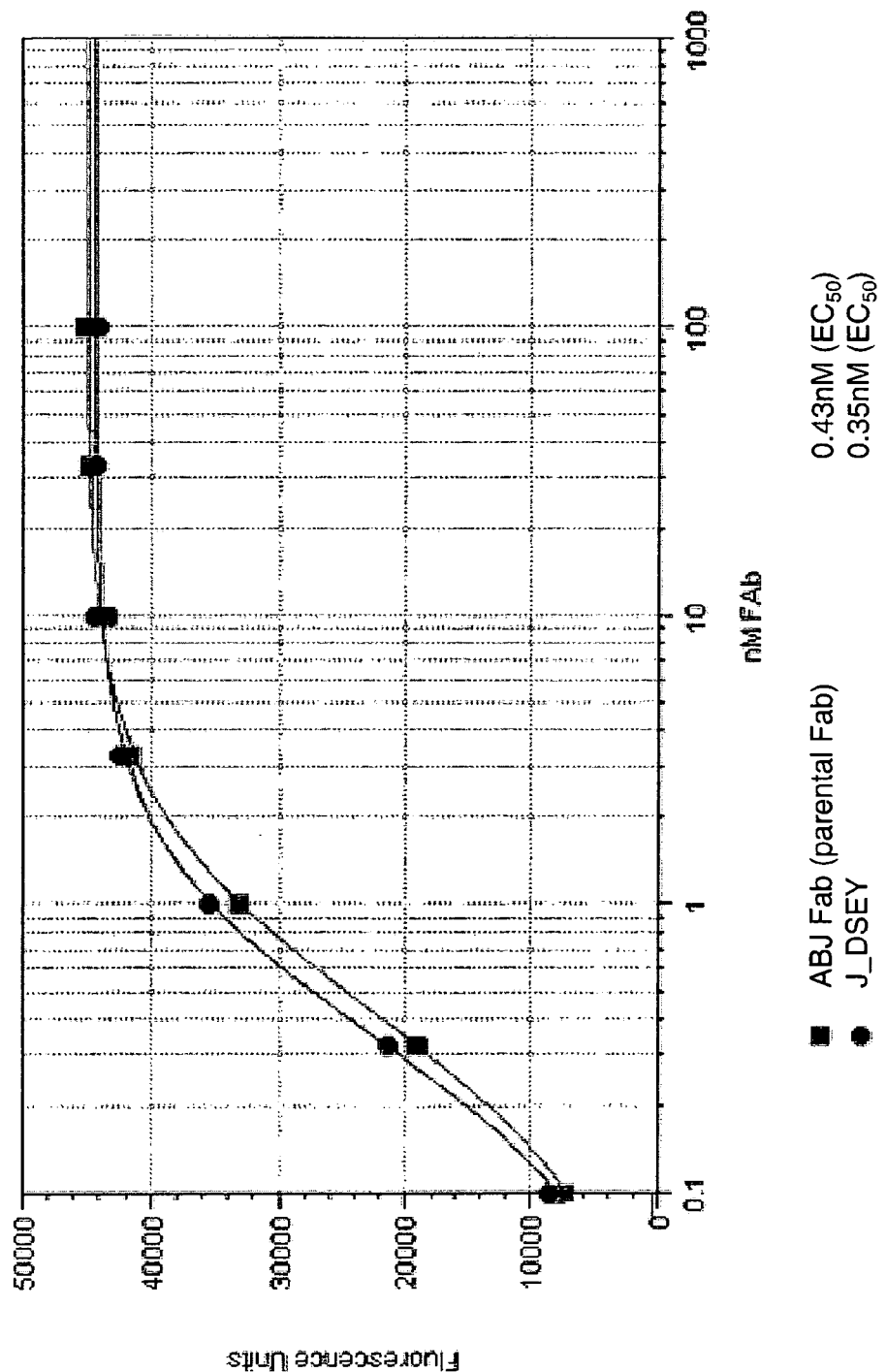
FIG. 11. Binding of the J_DSEY dimeric molecular complex to the biotinylated antigen protein for antibody ABJ protein compared with the binding of the Fab form of ABJ. The J_DSEY dimeric molecular complex and the Fab form of ABJ have equivalent activity, with an $EC_{50}$ that is approximately nanomolar. Previous studies comparing the monomeric Fab and dimeric IgG forms of ABJ in similar assays show that the monomeric and dimeric antibodies bind at similar concentrations. Antibody concentrations were calculated based upon molecular weights of 125 kD for the dimeric molecular complex, 50 kD for the Fab and 150 kD for the IgG. The secondary antibody used in the assay was HRP-anti-human Fab antibody (Jackson ImmunoReserch).
Figure 12:
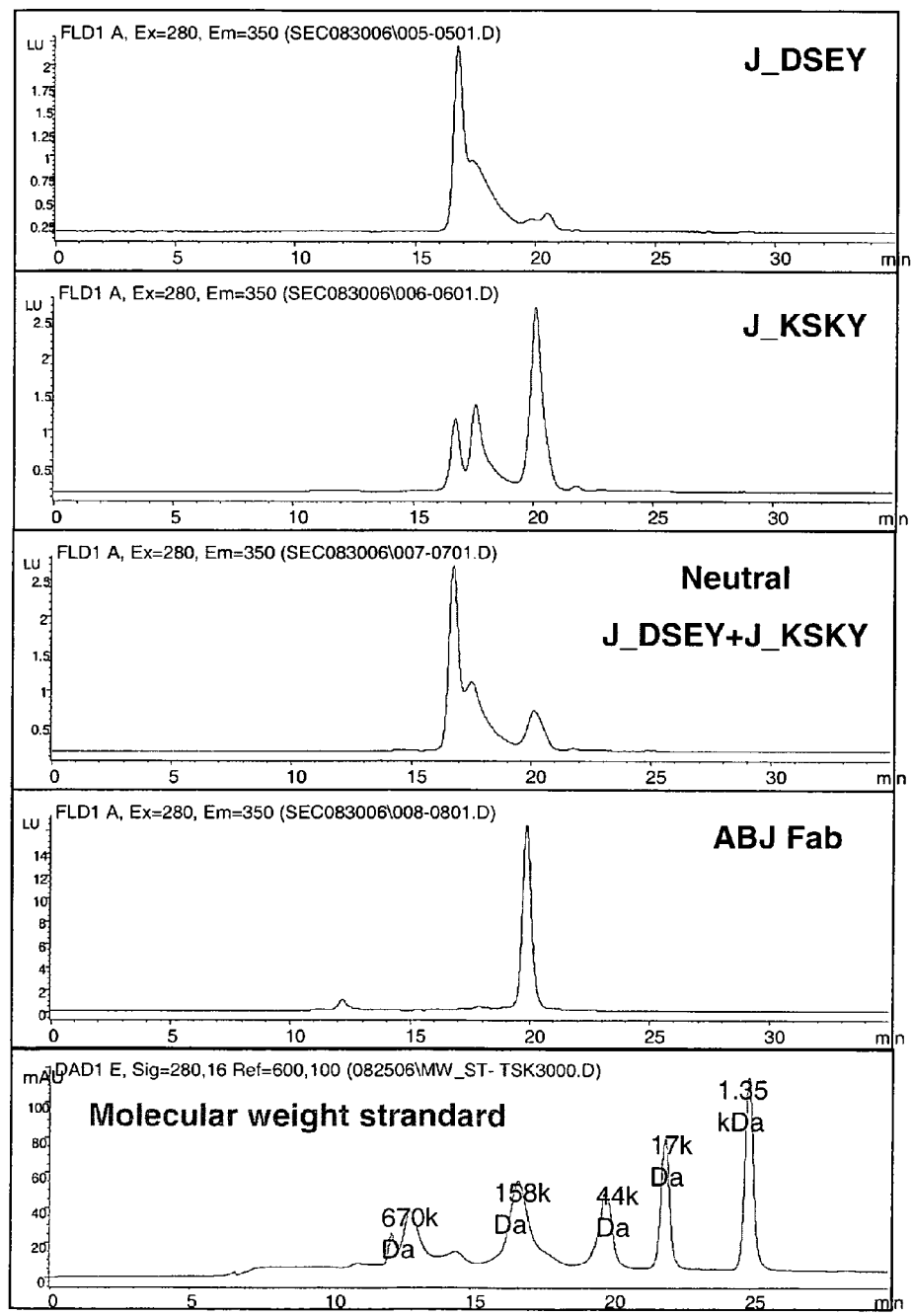
FIG. 12 Size exclusion chromatography (SEC) analysis. Both the J_DSEY dimeric molecular complex and the heterogeneous expression of J_DSEY and J_KSKY gave major peak at about 125 kD, suggesting the formation of dimeric complex. The J_KSKY dimeric molecular complex also showed a peak at about 125 kD although it is not the major peak.
Figure 13:
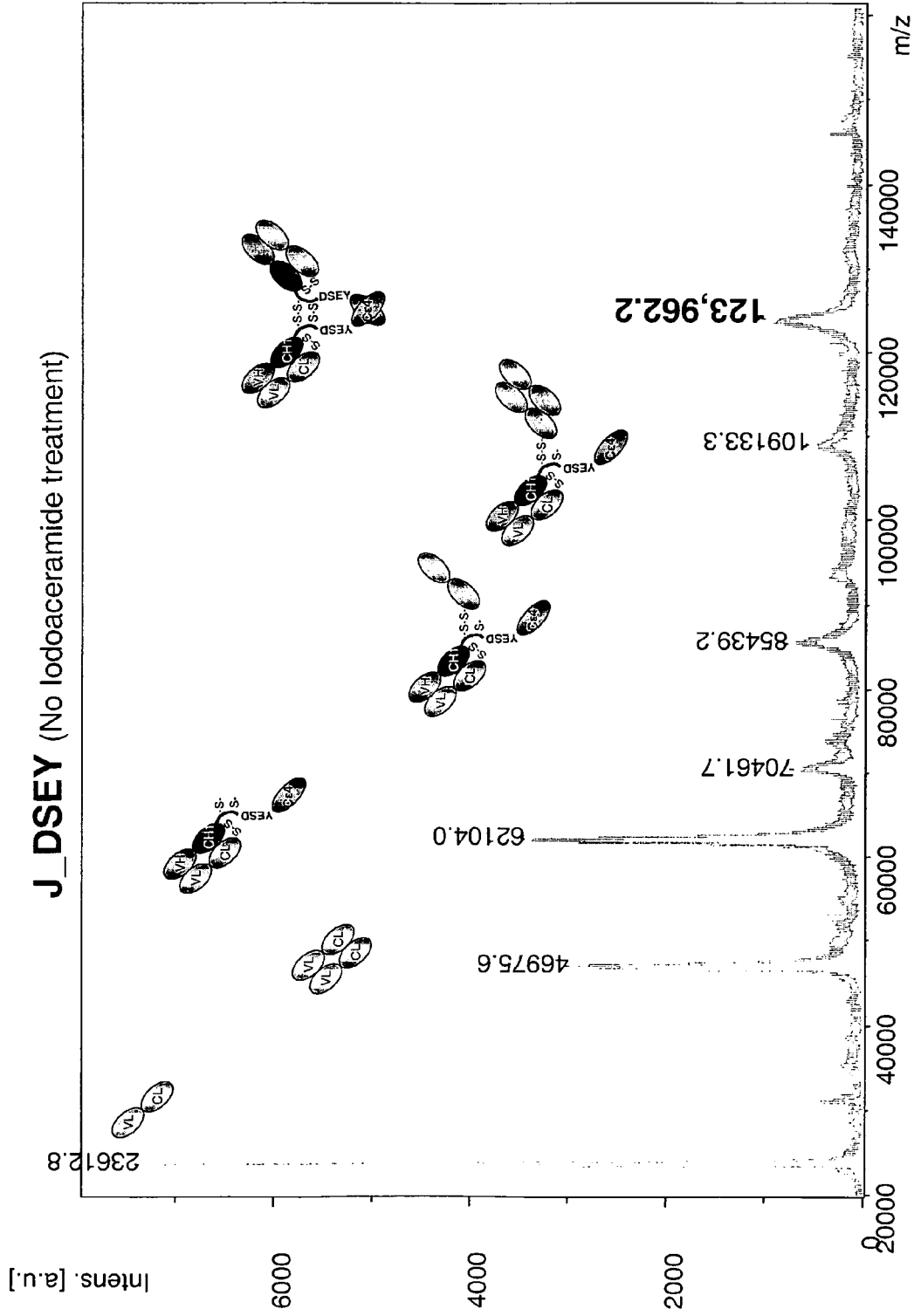
FIG. 13. MALDI-TOF Mass analysis. The J_DSEY dimolecular complex (0.26 mg/mL) was mixed with 10 mg/mL Sinapinic Acid MALDI Matrix in 50% Acetonitrile, 0.1% TFA at a ratio between 1:1 and 1:5 and 1 pmole minimum protein was targeted per spot. MALDI-TOF mass analysis was performed using a Bruker UTT instrument calibrated linearly with Bruker Protein Standards II. Positive ion spectra were recorded with an accelerating potential of 25 kV for 100 laser shots, accumulated for 15 events. The indicated molecular mass of 123,962.2 Da shown agrees with the molecular weight expected for the intact J_DSEY Fab dimeric molecular complex and is consistent with the SEC and calculated mass.

The entire heavy chain complex was amplified by PCR using primers which introduced an Xma restriction site, and then cloned by restriction digestion (BlpI and XmaI) into an IgG$_1$ expression vector, pIE_ABJ to produce the vector pIE-J_DSEY. See FIG. 10

```
ATG75 forward primer:
                                      (SEQ ID NO: 35)
CAGGTGCAATTGGTTCAGAGCG;

ATG76 reverse primer:
                                      (SEQ ID NO: 36)
CGACTCCCGGGTTACTATTTACCGGGATTTACAGACAC.
```

(b) Generation of a Second Heavy Chain Fab Fusion Protein

A second Fab dimeric molecular construct with a different (more basic) IgG$_1$ hinge domain was generated from the J_DSEY dimer heavy chain and IgE CH$_4$ domain (SEQ ID NO:20) by replacing the amino acids Asp, Ser, Glu and Tyr at positions 263 to 266 of SEQ ID NO:20 with Lys, Ser, Lys and Tyr (KSKY) using the QuikChange II Site-Directed Mutagenesis Kit provided by Stratagene and an appropriate set of primers.

```
ATG85 forward primer:
                                      (SEQ ID NO: 37)
GGGGGACCGTCAAAAAGCAAATACCCGCCGCGTGC;

ATG86 reverse primer:
                                      (SEQ ID NO: 38)
GCACGCGGCGGGTATTTGCTTTTTGACGGTCCCCC;
``` producing the vector pIE-J_KSKY.

EXAMPLE 6

Expression and Purification of the J_DSEY and J_KSKY Fab Dimeric Molecular Complexes The J_DSEY and J_KSKY Fab heavy chain fusion protein constructs described in Example 5 were each cloned into the mammalian expression vector pIE-ABK and expressed in CH0-K1 cells. Purification of each expression product was carried out using Protein L affinity chromatography, and the purified complexes were tested for binding, antigen specificity and affinity using an ELISA. The molecular weight of the purified complexes was analyzed in an SDS-PAGE system under reducing conditions (4%-12% SDS-PAGE, with a running buffer of MOPS SDS at 60 minutes at 120 mA, 200V) and were shown to possess the predicted molecular weight.

EXAMPLE 7

Production of Another Heavy Chain Fab Fusion Protein

Another Fab dimeric molecular complex using an antibody to the same antigen (AB25) was produced.

The heavy chain variable region of AB25 (SEQ ID NO:42) was cloned by PCR using primers which introduced a MfeI restriction site, and inserted by restriction digestion (NotI and BlpI) into the pIE-J_DSEY expression vector.

```
ATG 105 forward primer:
                                      (SEQ ID NO: 39)
GCGCGGCCGCGCCACCATGAAACACCTGTGGTTCTTCCTCCTGCTGGTG
GCAGCTCCCAGATGGGTCCTGTCCCAGGTGCAATTGGTTCAGAGCGGCG
CG;

ATG106 reverse primer:
                                      (SEQ ID NO: 40)
CCTTTGGTCGACGCTGAGCT;
```

The light chain variable region of AB25 (SEQ ID NO:44) was inserted by restriction digestion (EcoRI and BsiWI) into the pIE-J_DSEY expression vector.

EXAMPLE 8

Expression and Purification of the 25_DSEY Fab Dimeric Molecular Complex

Figure 14:
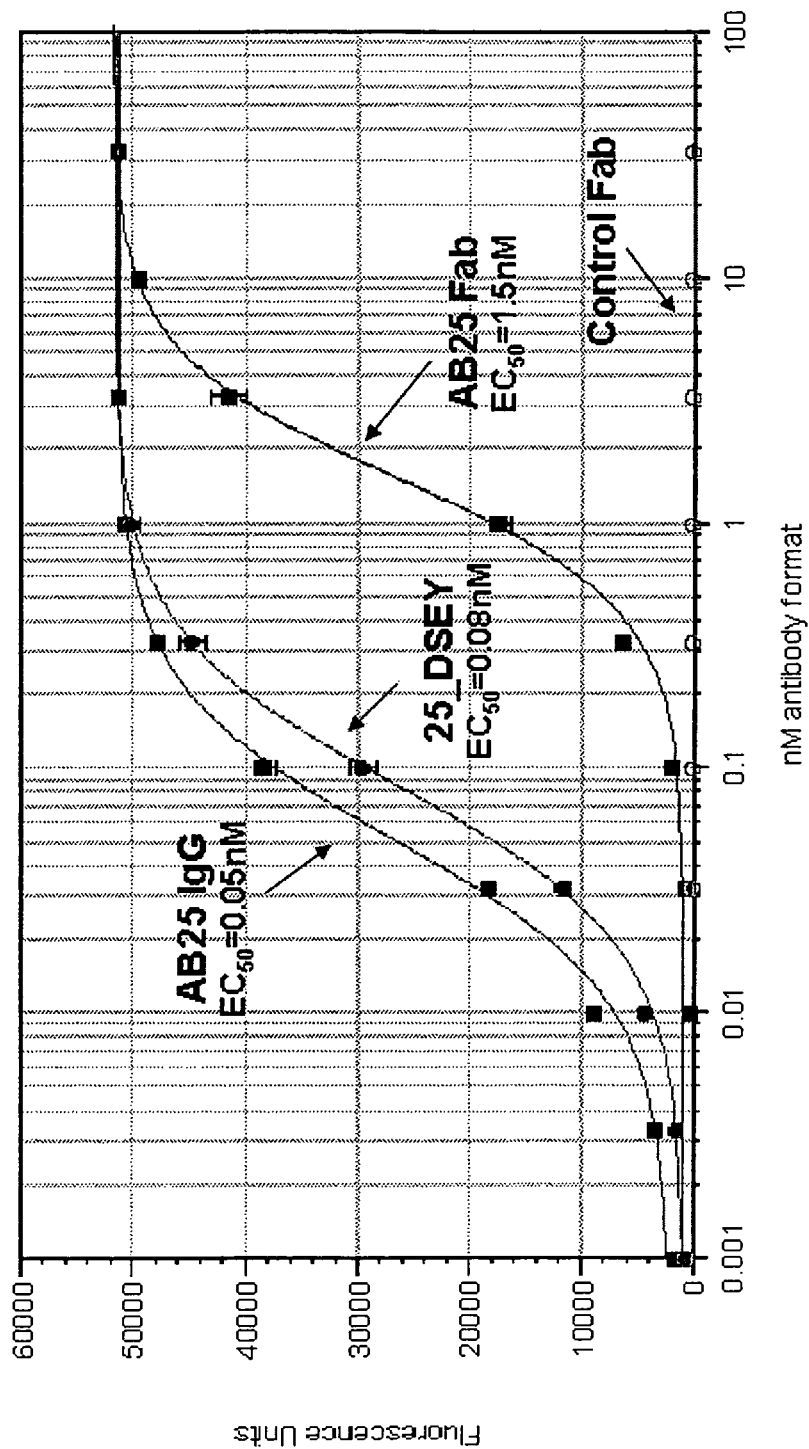
FIG. 14. Binding of the 25_DSEY dimeric molecular complex to biotinylated antigen protein for both antibody AB25 (same as antigen for ABJ above) compared with the binding of the Fab form of AB25 and the IgG form of AB25. The binding activity of the dimeric molecular complex (25_DSEY) was improved compared to that of the Fab, and equivalent to the binding found with the IgG form. The $EC_{50}$'s for the dimeric 25_DSEY Fab dimer and the IgG are both in the sub-nanomolar range. Previous studies comparing the monomeric Fab and dimeric IgG forms of AB25 in similar assays show that the dimeric IgG bound with greater avidity than did the monomeric Fab, consistent with these results. The antibody concentration was calculated based upon molecular weights of 125 kD for the dimeric molecular complex, 50 kD for the Fab and 150 kD for the IgG. The same HRP-anti-human Fab antibody as shown in Example 6 was used as a secondary antibody.

The 25_DSEY Fab dimeric molecular complex construct described in Example 7 was expressed in CH0-K1 cells. Purification was carried out using Protein L affinity chromatography, and the purified complex was tested for binding, antigen specificity, and affinity using an ELISA. The molecular weight of the purified complex was analyzed in an SOS-PAGE system under reducing conditions and was shown to possess the predicted molecular weight. As expected, the binding activity of the dimeric molecular complex (25_DSEY) was improved compared to that of the Fab, and equivalent to the binding found with the IgG form. The EC$_{50}$'s for the dimeric 25_DSEY Fab dimer and the IgG are both in the sub-nanomolar range. Previous studies comparing the monomeric Fab and dimeric IgG forms of AB25 in similar assays show that the dimeric IgG bound with greater avidity than did the monomeric Fab, consistent with these results. See FIG. 14.

We claim:

1. A dimeric molecular complex comprising a first and a second fusion protein, wherein each fusion protein comprises from its N to C terminus:
   (A) a biological effector moiety selected from the group consisting of:
      (1) a single chain antibody; and
      (2) an Fab fragment;
   (B) a hinge region of an IgG molecule bound to the biological effector moiety; and
   (C) a $CH_4$ dimerization domain of an IgE molecule covalently bound to the hinge region, wherein the molecular complex comprises a disulfide bond between a cysteine residue in the hinge region of the first fusion protein and a cysteine residue in the hinge region of the second fusion protein.

2. The molecular complex of claim 1, wherein the biological effector moieties of the first and second fusion proteins are identical.

3. The molecular complex of claim 1, wherein the biological effector moieties of the first and second fusion proteins are different.

4. The molecular complex of claim 1, wherein the biological effector moieties of the first and second fusion proteins each comprise an antigen binding site.

5. The molecular complex of claim 4, wherein the two antigen binding sites have the same specificity.

6. The molecular complex of claim 4, wherein the two antigen binding sites have different specificities.

7. The molecular complex of claim 1, wherein the hinge region of both the first and second fusion proteins is from an $IgG_1$ molecule.

8. The molecular complex of claim 7, wherein the hinge region comprises amino acid residues 223 to 243 of SEQ ID NO:25.

9. The molecular complex of claim 7, wherein within the hinge region of at least one of the two fusion proteins, the tetrapeptide VFLF, which occupies positions 240-243 in the IgG1 hinge region (SEQ ID NO:25), is replaced with a tetrapeptide selected from the group consisting of DSEY (SEQ ID NO:47), KSKY (SEQ ID NO:48), DEEY (SEQ ID NO:49), KRKY (SEQ ID NO:50), SESE (SEQ ID NO:51), SDSD (SEQ ID NO:52), SKSK (SEQ ID NO:53), SRSR (SEQ ID NO:54), SESY (SEQ ID NO:55), SDSY (SEQ ID NO:56), SKSY (SEQ ID NO:57), SRSY (SEQ ID NO:5), DDDY (SEQ ID NO:59), DDEY (SEQ ID NO:60), DEDY (SEQ ID NO:61), EEEY (SEQ ID NO:62), EDDY (SEQ ID NO:63), EDEY (SEQ ID NO:64), EEDY (SEQ ID NO:65), RRRY (SEQ ID NO:66), RKRY (SEQ ID NO:67), RRKY (SEQ ID NO:68), RKKY (SEQ ID NO:69), KKKY (SEQ ID NO:70), KRRY (SEQ ID NO:71), and KKRY (SEQ ID NO:72).

10. The molecular complex of claim 9, wherein the tetrapeptide is selected from the group consisting of DSEY (SEQ ID NO:47), KSKY (SEQ ID NO:48), DEEY (SEQ ID NO:49), and KRKY (SEQ ID NO:50).

11. The molecular complex of claim 10, wherein the tetrapeptide is DSEY (SEQ ID NO:47).

12. The molecular complex of claim 10, wherein the tetrapeptide is KSKY (SEQ ID NO:48).

13. The molecular complex of claim 9, wherein the tetrapeptide VFLF (SEQ ID NO:46) within the hinge region of both the first and second fusion proteins is replaced with the same tetrapeptide.

14. The molecular complex of claim 13, wherein the replacement tetrapeptide is selected from the group consisting of DSEY (SEQ ID NO:47), KSKY (SEQ ID NO:48), DEEY (SEQ ID NO:49), and KRKY (SEQ ID NO:50).

15. The molecular complex of claim 9, wherein the tetrapeptide VFLF (SEQ ID NO:46) within the hinge region of each of the first and second fusion proteins is replaced with a different tetrapeptide.

16. The molecular complex of claim 15, wherein the tetrapeptide VFLF (SEQ ID NO:46) within the hinge region of the first fusion protein is replaced with the tetrapeptide DSEY (SEQ ID NO:47) and within the hinge region of the second fusion protein is replaced with the tetrapeptide KSKY (SEQ ID NO:48).

17. The molecular complex of claim 12, further comprising a moiety covalently bound to a lysine in the hinge region, wherein the moiety is a toxin or a polyglycol.

18. The molecular complex of claim 1, further comprising an epitope tag at its C terminus.

19. The molecular complex of claim 18, wherein the epitope tag comprises GAPVPYPOPLEPRAA (SEQ ID NO:23).

20. The molecular complex of claim 1, further comprising an M2" IgE splice variant having the sequence of SEQ ID NO:26 at the C terminus of the first fusion protein and a different M2" IgE splice variant having the sequence of SEQ ID NO:27 at the C terminus of the second fusion protein.

21. The molecular complex of claim 1, further comprising an amino acid linker between the biological effector moiety and the hinge region, wherein the linker is covalently bound to the C-terminus of the effector moiety and the N-terminus of the hinge region.

22. The molecular complex of claim 5, wherein both the first and second fusion proteins are encoded by the nucleotide sequence of SEQ ID NO:22.

23. The molecular complex of claim 22, wherein amino acid residues at positions 263 to 267 of SEQ ID NO:20 are replaced with amino acid residues KTSG (residues 315-318 of SEQ ID NO:45) or with amino acid residues TKTSG (residues 314-318 of SEQ ID NO:45).

24. A composition comprising:
the dimeric molecular complex of claim 1 or 23; and
a pharmaceutically acceptable vehicle.

25. A dimeric molecular complex comprising a first and a second fusion protein,
wherein each fusion protein comprises from its N to C terminus:
(A) a biological effector moiety selected from the group consisting of:
(1) a single chain antibody; and
(2) an Fab fragment;
(B) a hinge region of an IgG molecule bound to the biological effector moiety; and
(C) a $CH_4$ dimerization domain of an IgE molecule covalently bound to the hinge region, wherein the molecular complex comprises a disulfide bond between a cysteine residue in the hinge region of the first fusion protein and a cysteine residue in the hinge region of the second fusion protein and wherein the biological effector moieties of the first and second fusion proteins each comprise an antigen binding site, wherein the two antigen binding sites have the same specificity, and wherein both the first and second fusion proteins comprise the amino acid sequence of SEQ ID NO:1.

26. A dimeric molecular complex comprising a first and a second fusion protein,
wherein each fusion protein comprises from its N to C terminus:
(A) a biological effector moiety selected from the group consisting of:
(1) a single chain antibody; and
(2) an Fab fragment;
(B) a hinge region of an IgG molecule bound to the biological effector moiety; and
(C) a $CH_4$ dimerization domain of an IgE molecule covalently bound to the hinge region, wherein the molecular complex comprises a disulfide bond between a cysteine residue in the hinge region of the first fusion protein and a cysteine residue in the hinge region of the second fusion protein and wherein the biological effector moieties of the first and second fusion proteins each comprise an antigen binding site, wherein the two antigen binding sites have the same specificity, and wherein both the first and second fusion proteins comprise the amino acid sequence encoded by the sequence of SEQ ID NO:2.

27. The molecular complex of claim 25, wherein the amino acid residues at positions 277-281 of SEQ ID NO:1 (OSEYP) are replaced with amino acid residues KTSG (residues 315-318 of SEQ ID NO:45) or with amino acid residues TKTSG (residues 314-318 of SEQ ID NO:45).

* * * * *